US007301005B2

(12) United States Patent
Albani et al.

(10) Patent No.: US 7,301,005 B2
(45) Date of Patent: Nov. 27, 2007

(54) IMMUNOMODULATORY PEPTIDES DERIVED FROM HEAT SHOCK PROTEINS AND USES THEREOF

(76) Inventors: Salvatore Albani, 629 Fourth St., Encinitas, CA (US) 92024; Dennis A. Carson, 14824 Vista del Oceano, Del Mar, CA (US) 92014; Berent J Prakken, Pieter Saenredamstraat 13, 3585 TA Utrecht (NL); Alberto Martini, Via 6.Taverna 25, 29100 Piacenza (IT)

( * ) Notice: Subject to any disclaimer, the term of this patent is extended or adjusted under 35 U.S.C. 154(b) by 21 days.

(21) Appl. No.: 10/001,938

(22) Filed: Oct. 31, 2001

(65) Prior Publication Data

US 2003/0031679 A1 Feb. 13, 2003

Related U.S. Application Data

(60) Provisional application No. 60/245,181, filed on Nov. 1, 2000.

(51) Int. Cl.
*C07K 5/00* (2006.01)
(52) U.S. Cl. .................. 530/326; 514/2; 424/185.1
(58) Field of Classification Search ............. 424/185.1, 424/192.1; 514/2, 8; 530/326, 300, 350
See application file for complete search history.

(56) References Cited

U.S. PATENT DOCUMENTS

| | | | |
|---|---|---|---|
| 4,654,419 A | | 3/1987 | Vaughan et al. |
| 4,683,295 A | | 7/1987 | Carson |
| 4,732,757 A | | 3/1988 | Stolle et al. |
| 5,116,725 A | | 5/1992 | Vaughan et al. |
| 5,310,732 A | | 5/1994 | Carson et al. |
| 5,334,379 A | * | 8/1994 | Pillai et al. ............... 424/85.2 |
| 5,541,164 A | | 7/1996 | Carson et al. |
| 5,728,385 A | | 3/1998 | Classen |
| 5,773,570 A | * | 6/1998 | Carson et al. ........... 424/201.1 |
| 5,891,435 A | | 4/1999 | Muir et al. |
| 5,992,567 A | | 7/1999 | Au-Young et al. |
| 5,993,803 A | | 11/1999 | Cohen et al. |
| 6,007,821 A | | 12/1999 | Srivastava et al. |

FOREIGN PATENT DOCUMENTS

| WO | WO90/14835 | 12/1990 |
|---|---|---|
| WO | WO95/31984 | 11/1995 |
| WO | WO 9832772 A1 * | 7/1998 |

OTHER PUBLICATIONS

Immunology. Kuby, 1992 W. H. Freeman and Company, p. 74.*
Fernandes et al. Characterization of MHC class II-presented peptides generated from an antigen targeted to different endocytic compartments, Eur. J. Immunol. 2000, 30:2333-2343.*
Link et al., J. Biol. Chem., 2006, 281:1808-1816.*
Albani et al., "Positive selection in autoimmunity: Abnormal immune response to a bacterial dnaJ antigenic determinant in patients with early rheumatoid arthritis," Nature Medicine, 1 (5):448-452, 1995.
McColl et al., "Absence of peripheral blood T cell responses to 'shared epitope' containing peptides in recent onset rheumatoid arthritis," *Anals Rheum Dis*, 56:240-246 (1997).
McSorely et al., "Selective tolerization of Th1-like cells after nasal administration of a cholers toxoid-LACK conjugate," Eur. J. Immunol., 28:424-432 (1998).
Vandenbark et al., "Differential susceptibility of human $T_h1$ versus $T_h2$ cells to induction of anergy and apoptosis by EDCI/antigen-coupled antigen-presenting cells," *International Immunology*, 12 (1):57-66 (1999).
Bonnin, D., et al., "MHC-Derived Peptides Drive Positive T Cell Selection in the Thymus: from a Physiological System to an HLA DRB1*0401 Transgenic Mouse Model for Rheumatoid Arthritis?", *Arthritis and Rheumatism*, vol. 39, No. 9 Suppl., p. S160, Oct. 1996.
Auger, I., et al., "HLA-DR4 and HLA-DR10 Motifs that Carry Susceptibility to Rheumatoid Arthritis Bind 70-kD Heat Shock Proteins," *Nature Medicine*, vol. 2, No. 3, pp. 306-310, Mar. 1996.
Albani, et al., "Genetics and Environmental Factors in the Immune Pathogenesis of Rheumatoid Arthritis," *Rheumatic Disease Clinics of North America*, 18/4:729-740, 1992.
Stastney, P., et al., "Immunogenetics of Rheumatoid Arthritis and Juvenile Arthritis", *Recenti Progressi in Medicina*, vol. 82, No. 7-8, pp. 409-416, 1991.
Nepom, G., "Prediction of Susceptibility to Rheumatoid Arthritis by Human Leukocyte Antigen Genotying" *Rheumatic Disease Clinics of North America*, vol. 18, No. 4, pp. 785-792, Nov. 1992.
Weyand, C., et al., "The Influence of HLA-DRB1 Genes on Disease Severity in Rheumatoid Arthritis," Annals of Internal Medicine, vol. 117, No. 10, pp. 801-806, Nov. 15, 1992.
Fairchild, P., et al., "Peptide-MHC Interaction in Autoimmunity," *Current Opinion in Immunology*, vol. 4, pp. 748-753, 1992.
Life, P.F., et al., "Synovial Fluid Antigen-Presenting Cells Unmask Peripheral Blood T Cell Responses to Bacterial Antigens in Inflammatory Arthritis," *Clin. Exp. Immunol.* vol. 79, pp. 189-194, 1990.
Van Den Broek, M.F., et al., "Protection Against Streptococcal Cell Wall-Induced Arthritis by Pretreatment with the 65-kD Mycobacterial Heat Shock Protein," *J. Exp. Med.*, vol. 170, pp. 449-466, Aug. 1989.

(Continued)

*Primary Examiner*—G. R. Ewoldt
*Assistant Examiner*—Michael Szperka
(74) *Attorney, Agent, or Firm*—DLA Piper US LLP

(57) ABSTRACT

A method of modulating an immune response in a subject is disclosed. The invention is based on the discovery that an effective therapeutic strategy for ameliorating the inflammation-related symptoms of an immune-mediated disease, such as arthritis, can be achieved by modulation of the underlying immune response itself, rather than by merely addressing the resulting inflammation. This strategy can be used to regulate the inflammatory response and is applicable to a variety of contexts in which immune modulation is desired, such as mucosal tolerization, DNA vaccination, anergy induction, active immunization, and ex vivo modulation of antigen-specific T cells. In one embodiment, the method comprises administering to the subject a bacterial dnaJ peptide or a human homolog or a non-homologous human isoform thereof.

5 Claims, 14 Drawing Sheets

OTHER PUBLICATIONS

Anderton, S.M., et al. "Activation of T Cells Recognizing Self 60-kD Heat Shock Protein Can Protect Against Experimental Arthritis,"*J. Exp. Med.*, vol. 181, pp. 943-952, Mar. 1995.

Albani, S., et al., "A Multistep Molecular Mimicry Hypothesis for the Pathogenesis of Rheumatoid Arthritis," *Immunology Today*, vol. 17, No. 10, pp. 466-470, Oct. 1996.

Anderton et al, "Differential Mycobacterial 65-kDa Heat Shock Protein T Cell Epitope Recognition after Adjuvant Arthritis-Inducing or Protective Immunization Protocols[1]," *J. Immunology* 152:3656-64, 1994.

Albani et al, "HLA Binding Studies Support a Role for the QKRAA Susceptibility Sequence to Rheumatoid Arthritis (RA) in Positive Selection and Activation of Pathogenic T Lymphocytes," *Arthritis and Rheumatism*, 38/9 Suppl., p. S181, Abstract#173, 1995.

Plotkin, S.A., et al., "New Technologies for Making Vaccines," *Vaccines*, pp. 568-575, 1988.

Albani, S., et al., "Molecular Basis for the Association Between HLA DR4 and Rheumatoid Arthritis. From the Shared Epitope Hypothesis to a Peptidic Model of Rheumatoid Arthritis," *Clin. Biochem.* vol. 25, pp. 209-212, 1992.

La Cava, A., et al., "The QKRAA Disease Susceptibility Sequence for Rheumatoid Arthritis (RA) is a B Cell Epitope Shared by the Epstein-Barr Virus (EBV) Protein gp110 and the *E. coli* Heat Shock Protein dnaJ Possible Implications for Disease Pathogenesis," *Arthritis & Rheum.* 36(9) Suppl. pp. S127 Abstract 1993.

Asseldonk, M., et al., "Cloning, Nucleotide Sequence, and Regulatory Analysis of the *Lactococcus lactic dnaJ* Gene,", *Journal of Bacteriology*, 175(6), pp. 1637-1644, Mar. 1993.

Bardwell, J.C.A., et al., "The Nucleotide Sequence of the *Escherichia coli K12 dnaJ+* Gene," *The Journal of Biological Chemistry*, vol. 261, No. 4, pp. 1782-1785, Feb. 5, 1986.

Ohki, M., et al., "Nucleotide Sequence of the *Escherichia coli dnaJ* Gene and Purification of the Gene Product*", The Journal of Biological Chemistry, vol. 261, No. 4, pp. 1778-1781, 1986.

Albani, S., et al., "The Susceptibility Sequence to Rheumatoid Arthritis is a Cross-Reactive B Cell Epitope Shared by the *Escherichia coli* Heat Shock Protein dnaJ and the Histocompatibility Leukocyte Antigen DRB10401 Molecule," *J. Clin. Invest.*, vol. 89, pp. 327-331, 1992.

van Eden, W., et al., "Cloning of the Mycobacterial Epitope Recognized by T Lymphocytes in Adjuvant Arthritis," *Nature*, vol. 331, pp. 171-173, Jan. 14, 1988.

Silver, P.A., et al. "Eukaryotic DnaJ Homologs and the Specificity of Hsp70 Activity," *Cell*, vol. 74, pp. 5-6, Jul. 16, 1993.

Zuber et al., "Cloning, Sequencing and Expression of the *dnaJ* gene of *Coxiella burnetii*," *Gene*, vol. 152 pp. 99-102, 1995.

DeGraeff-Meeder, E.R., et al., "Recognition of Human 60kD Heat Shock Protein by Mononuclear Cells from Patients with Juvenile Chronic Arthritis," *The Lancet*, vol. 337, pp. 1368-1372, Jun. 8, 1991.

Brackertz et al, "OM-8980 in Rheumatoid Arthritis: A 6-Month Double Blind Placebo Controlled Multicenter Study," *Journal of Rheumatology*, vol. 16, pp. 19-23, 1989.

Marsh, S.G.E., et al, "HLA Class II Nucleotide Sequences, 1991," *Tissue Antigens*, vol. 37, pp. 181-189, 1991.

Albani, S., et al., "Immune Responses to the *Escherichia coli* dnaJ Heat Shock Protein in Juvenile Rheumatoid Arthritis and their Correlation with Disease Activity," *The Journal of Pediatrics*, vol. 124, No. 4, pp. 561-565, Apr. 1994.

Gencore Accession #HHECDJ; Date: Jan. 30, 1988; revised Mar. 1, 2002.

* cited by examiner

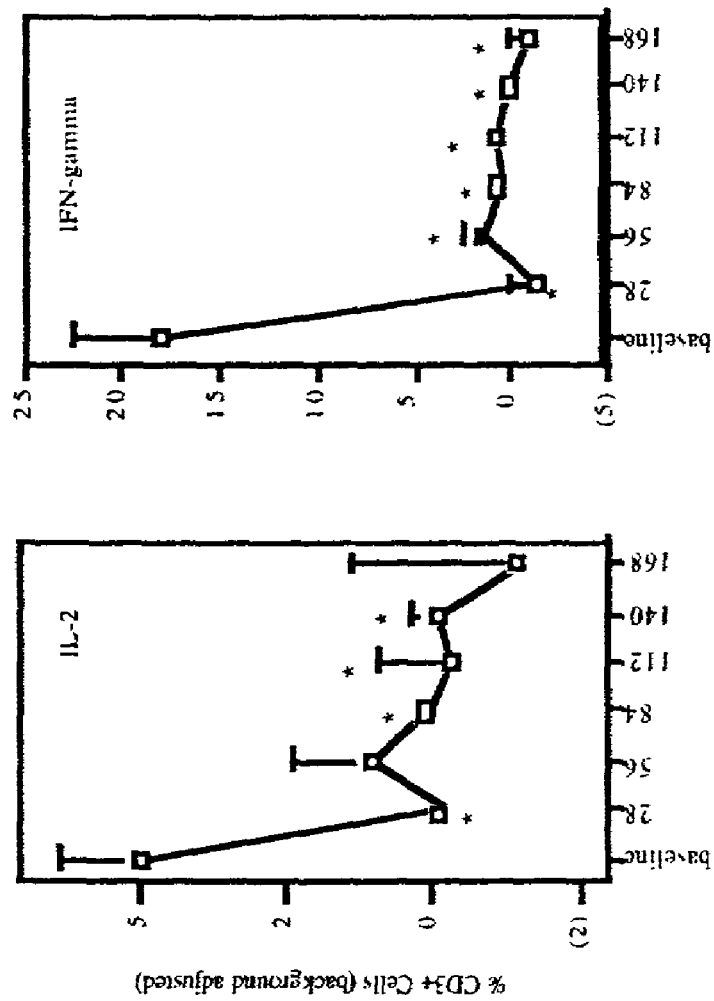
Figure 26c
Figure 26b
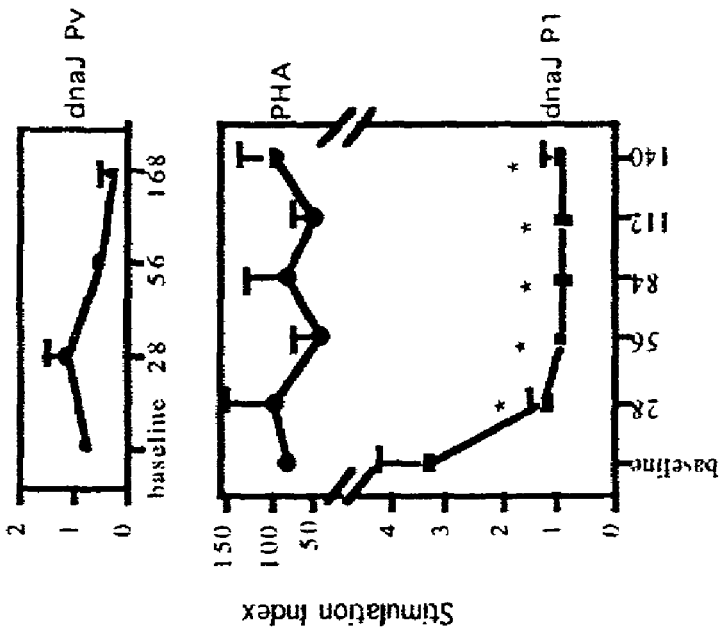
Figure 26a

IMMUNOMODULATORY PEPTIDES DERIVED FROM HEAT SHOCK PROTEINS AND USES THEREOF

This application claims the benefit under 35 U.S.C. 119(e) of U.S. Ser. No. 60/245,181, filed Nov. 1, 2000, the entire contents of which is incorporated herein by reference.

This invention was made with Government support under Grant No. AR44850, awarded by the National Institutes of Health. The government has certain rights in this invention.

BACKGROUND OF THE INVENTION

1. Field of the Invention

The present invention relates generally to methods and compositions for modulating an immune response in a subject, and more specifically to compositions containing a bacterial dnaJ peptide or a human homolog or a non-homologous human isoform thereof, and to methods of using such compositions to stimulate an immune response or to generate tolerance to an immunogen. As such, the present invention provides various means to regulate an inflammatory response, including methods of mucosal tolerization, DNA vaccination, anergy induction and active immunization.

2. Background Information

Treatment strategies for many diseases are directed at alleviating the symptoms of the disease rather than resolving the cause of the problematic symptoms. In the case of inflammatory diseases, for example, most treatments are directed to relieving the inflammation generally such as by using steroidal or non-steroidal anti-inflammatory agents.

Inflammation often occurs as a result of an immune response. Although an immune response and the consequent inflammatory response generally provide an advantage to an individual, for example, where the response is to a bacterial infection, in some cases an immune response and inflammatory response produce deleterious consequences. In particular, patients with an auto-immune diseases such as rheumatoid arthritis, systemic lupus erythematosis, and the like, often suffer from severe and in some cases generalized tissue damage. Although administration of a steroidal drug, for example, can decrease the severity of the immune response is such patients, the long term use of such drugs can produce adverse effects, including decreasing the patient's quality of life. Furthermore, the use of such drugs generally reduces the ability of an individual to mount an immune response, thus leaving the individual susceptible to short term infections that can produce severe consequences. Thus, a need exists for compositions and methods that are useful for specifically modulating an immune response, and the associated inflammatory response. The present invention satisfies this need and provides additional advantages.

SUMMARY OF THE INVENTION

The present invention relates to immunogenic peptides derived from a dnaJ heat shock protein (hsp), and methods of using such peptides a method of modulating an immune response in a subject. As disclosed herein, the immunogenic peptides of the invention, which act via a T cell mediated immune response, include "pro-inflammatory peptides", which result in increased expression of pro-inflammatory cytokines such as interferon-gamma, and "anti-inflammatory peptides", which result in increased expression of anti-inflammatory cytokines such as interleukin-10. The peptides also can be characterized generally as "homologous peptides", which have an amino acid sequence that is relatively conserved among dnaJ hsp's of various species, and "non-homologous peptides", which have an amino acid sequence that is not substantially conserved.

Accordingly, the present invention relates to a method of modulating an immune response in a subject. A method of the invention can be performed, for example, by administering an immunogenic peptide portion of a dnaJ hsp to the subject, thereby modulating an immune response in the subject. The dnaJ hsp can be a prokaryotic or eukaryotic dnaJ hsp, including, for example, a bacterial dnaJ hsp such as an *E. coli* dnaJ hsp; an invertebrate dnaJ hsp such as a yeast dnaJ hsp; or a vertebrate dnaJ hsp such as a mammalian dnaJ hsp, including a human dnaJ hsp such as human HSJ1, HDJ1 or HDJ2.

The immunogenic peptide can be any immunogenic portion of the dnaJ hsp, including a glycosylated form of such a peptide, and generally is a peptide that can bind an MHC class II receptor or a T cell receptor, and that provides an epitope that is substantially specific for a dnaJ polypeptide. For example, the peptide can be an immunogenic peptide portion of an *E. coli* dnaJ hsp such as a peptide having the amino acid sequence QDYYEILGVSKTAEE (SEQ ID NO:1), RKAYKRLAMKYHPDR (SEQ ID NO:2), QKRAAYDQYGHAAFEQ (SEQ ID NO:3), QGF-FAVQQTCPHCQG (SEQ ID NO:4), SKTLSVKIP-GAVDTG (SEQ ID NO:5), GDLYVQVQVKQHPIF (SEQ ID NO:6), YCEVPINFAMAALGG (SEQ ID NO:7), or PINFAMAALGGEIEV (SEQ ID NO:8); or an immunogenic of a human HSJ1, HDJ1 or HDJ2 dnaJ hsp such as a peptide having the amino acid sequence ASYYEILD-VPRSASA (SEQ ID NO:9), KDYYQTLGLARGASD (SEQ ID NO:10), TTYYDVLGVKPNATQ (SEQ ID NO:11), KKAYRRKALQWHPDK (SEQ ID NO:12), KRAYRRQALRYHPDK (SEQ ID NO:13), KKAYRKLA-LKYHPDK (SEQ ID NO:14), FRSVSTSTTFVQGRR (SEQ ID NO:15), PGMVQQIQSVCMECQ (SEQ ID NO:16), or GRRITTRRIMENGQE (SEQ ID NO:17), or a peptide having the amino acid sequence QAYEVLS-DAKKRELYD (SEQ ID NO:18), EAYEVLSDKHKREIYD (SEQ ID NO:19), SGPFFTFSSSFPGHS (SEQ ID NO:20), DGQLKSVTINGVPDD (SEQ ID NO:21), DLQLAMAY-SLSEMEA (SEQ ID NO:22), EDLFMCMDIQLVEAL (SEQ ID NO:23), LCGFQKPISTLDNRT (SEQ ID NO:24), RTIVITSHPGQIVKH (SEQ ID NO:25), or GRLIIEFKVN-FPENG (SEQ ID NO:26).

A method of the invention can modulate an immune response by increasing or decreasing an inflammatory response associated with the immune response. Thus, in one embodiment, a method of the invention provides a means for augmenting or inducing an inflammatory response in the subject. In one aspect, the method of augmenting or inducing an inflammatory response in the subject is performed by administering a peptide having pro-inflammatory activity, i.e., a pro-inflammatory peptide, to the subject under immunizing conditions. In another aspect, the method is performed by administering an anti-inflammatory peptide to the subject under tolerizing conditions. In still another aspect of the method, a combination of immunogenic peptides is administered, for example, two or more pro-inflammatory peptides under immunizing conditions, or two or more anti-inflammatory peptides under tolerizing conditions, or at least one pro-inflammatory peptide under immunizing conditions and at least one anti-inflammatory peptide under tolerizing conditions. Such a method of augmenting or inducing the inflammatory response results in an increase in the level of a pro-inflammatory cytokine such as interferon gamma (IFNγ), tumor necrosis factor-alpha (TNFα), interleukin-1 (IL-1), IL-6, IL-12, or IL-23, in the subject, or a decrease in the level of an anti-inflammatory cytokine such as IL-4, IL-10, or transforming growth factor-beta (TGFβ), in the subject, or combinations thereof.

In another embodiment, a method of the invention provides a means for reducing or inhibiting an inflammatory response in the subject. In one aspect, the method of reducing or inhibiting the inflammatory response is performed by administering a peptide having anti-inflammatory activity to the subject under immunizing conditions. In another aspect, the method is performed by administering a pro-inflammatory peptide to the subject under tolerizing conditions. In still another aspect, a combination of immunogenic peptides are administered, for example, two or more pro-inflammatory peptides under tolerizing conditions, or two or more anti-inflammatory peptides under immunizing conditions, or at least one pro-inflammatory peptides under tolerizing conditions and at least one anti-inflammatory peptide under immunizing conditions. Such a method of reducing or inhibiting the inflammatory response results in an increase in the level of an anti-inflammatory cytokine such as IL-4, IL-10, or TGFβin the subject, or a decrease in the level of a pro-inflammatory cytokine such as IFNγ, TNFα, IL-1, IL-6, IL-12, or IL-23, in the subject, or combinations thereof.

As disclosed herein, one or a combination of immunogenic peptide portions of a dnaJ hsp can be administered, including, for example, any one or any combination of the immunogenic peptides exemplified by SEQ ID NOS:1-26. As will be apparent from the present disclosure, a peptide of the invention is administered to a subject under immunizing conditions or under tolerizing conditions, depending on whether the peptide is a pro-inflammatory peptide or an anti-inflammatory peptide, and whether the peptide is being administered to augment or induce an inflammatory response or to reduce or inhibit an inflammatory response. A peptide can be administered under immunizing conditions by administering an immunogenic amount of the peptide, for example, intradermally, subcutaneously, or intramuscularly, and, if desired, in a composition that includes an immunoadjuvant such as Freund's complete or incomplete adjuvant. A peptide can be administered under tolerizing conditions by administering a tolerizing amount of the peptide, for example, mucosally, or intradermally, subcutaneously, or intramuscularly.

A method of the invention can be practiced with respect to a subject having, or predisposed or susceptible to, any condition in which it is desired to modulate an immune response, including a subject that has an immunologic disorder, or is susceptible or predisposed to an immunological disorder. The subject generally is a vertebrate subject, and particularly a mammal, including a domesticated animal such as a cat, a dog, or a horse; a farm animal such as an ovine, bovine or porcine animal; or a human. The immunological disorder can be a disorder of the immune system such as an autoimmune disease, for example, an arthritis such as oligoarticular juvenile idiopathic arthritis, or an immunodeficiency disease such as acquired immunodeficiency disease (AIDS). Additional conditions in which it can be desired to modulate the immune response include conditions in which the subject has not developed a sufficient immune response, for example, in response to an infectious disease or a cancer, or a condition in which the subject has too great of an immune response, for example, a subject suffering from an inflammatory bowel disease other than an auto-immune disease or a subject suffering from bacterial sepsis.

The present invention also relates to a method of modulating immunoeffector cell responsiveness. Such a method can be performed, for example, by contacting immunoeffector cells with a peptide portion of a dnaJ hsp to the subject. The dnaJ hsp from which the peptide is derived can be any dnaJ hsp as disclosed herein or otherwise known in the art, including, a prokaryotic or eukaryotic dnaJ hsp. The peptide can, but need not, be formulated in a composition, which also can contain, if desired, an immunoadjuvant or other immunomodulatory agent, for example, one or more cytokines. The immunoeffector cells, which can be any cells involved in a T cell mediated immune response, particularly T cells, can be contacted with the peptide in vivo by administering the peptide to a subject, or can be contacted in vitro.

Where immunoeffector cells are contacted in vitro (or ex vivo), the method can further include administering the contacted immunoeffector cells to a subject, thereby providing a means to modulate an immune response in the subject. As such, the immunoeffector cells can be autologous with respect to the subject, i.e., cells that have been removed from the patient, contacted with the peptide ex vivo, then administered to the subject, following expansion of the cells in culture, if desired. The immunoeffector cells also can be allogeneic with respect to the subject, for example, cells that are at least partially haplotype matched to the subject. Accordingly, such a method provides a means for modulating the immune response by augmenting or inducing an inflammatory response in the subject, or by reducing or inhibiting an inflammatory response in the subject.

The present invention also relates to an immunogenic peptide portion of a dnaJ hsp that has pro-inflammatory or anti-inflammatory activity. Such immunogenic peptides of the invention are exemplified by the peptides set forth as SEQ ID NOS:1 to 26. In addition, the present invention relates to a chimeric polypeptide, which includes a peptide of the invention operatively linked to at least one heterologous polypeptide. A composition containing at least one peptide of the invention is provided, for example, a composition containing any one of the peptides set forth as SEQ ID NOS:1-26, and a composition containing any combination of such peptides, particularly a composition containing a combination of pro-inflammatory peptides and a composition containing a combination of anti-inflammatory peptides. A composition of the invention generally is formulated in a physiologically acceptable solution and, if desired, can further contain one or more immunoadjuvants, for example, one or more cytokines, Freund's complete adjuvant, Freund's incomplete adjuvant, alum, or the like. Generally, where the composition contains one or more cytokines, the cytokines an inflammatory activity that is the same as or complements the inflammatory activity of the peptide of the invention.

The present invention further relates to a polynucleotide encoding an immunogenic peptide of the invention. The polynucleotide can be single stranded or double stranded, and can be a ribonucleic acid molecule (RNA), a deoxyribonucleic acid molecule (DNA), or a hybrid thereof. Also provided is a recombinant nucleic acid molecule, which includes a polynucleotide of the invention operatively linked to at least one heterologous nucleotide sequence. The heterologous nucleotide sequence can be any nucleotide sequence that is not normally found in contiguous linkage with the polynucleotide of the invention in nature. For example, the heterologous nucleotide sequence can be an expression control sequence such as a transcription regulatory element or a translation regulatory element, or a combination thereof; or can encode a polypeptide such as a cytokine or other immunomodulatory agent, a peptide tag, a cellular localization domain, or the like. Also provided is a vector containing a polynucleotide of the invention, for example, an expression vector, and cell that contain a polynucleotide or vector of the invention.

A method of modulating an immune response in a subject according to the present invention is based on the discovery that an effective therapeutic strategy for ameliorating the inflammation-related symptoms of an immune-mediated disease such as arthritis can be achieved by modulation of the underlying immune response, itself, rather than by merely addressing the resulting inflammation. This strategy can be used to regulate the inflammatory response and is applicable to a variety of contexts in which immune modulation is desired, including, for example, mucosal tolerization, DNA vaccination, anergy induction, active immunization, and ex vivo modulation of antigen-specific T cells.

In various embodiments, the modulating can include increasing the levels of pro-inflammatory cytokines such as IFNγ levels or TNFα in the subject; stimulating the proliferation of mononuclear cells; or increasing the levels of anti-inflammatory cytokines such as IL-10, IL-4 or TGFβ levels in the subject. In other embodiments, the modulating can include reducing or inhibiting cytokine levels in the subject. As such, a composition or method of the invention provides a means to enhance a pro-inflammatory response or a toleragenic response, as appropriate to the circumstances of the subject to be treated.

A method of the invention is useful for treating a subject suffering from a disease that involves or is mediated by an immune response, for example, an autoimmune disease, an infectious disease, or cancer. Examples of an autoimmune disease that can be treated according to a method of the invention include arthritis, particularly oligoarticular juvenile idiopathic arthritis (oJIA), diabetes and multiple sclerosis. A composition or method of the invention also can be useful as part of a combined modality treatment, for example, as an adjuvant to a cancer therapy or to a therapy directed at an infectious agent.

BRIEF DESCRIPTION OF THE FIGURES

FIG. 1A shows the proliferative responses of peripheral blood (PBMC) and synovial fluid mononuclear cells (SFMC) from healthy subjects ("CTRL") and patients with oligoai ticular juvenile idiopathic arthritis ("oJIA") stimulated with recombinant *E. coli* hsp dnaJ for 96 hours. Results, expressed as stimulation index (SI), are shown as mean+SD.

FIG. 1B provides an evaluation of CD69+ T cells from healthy subjects (CTRL) and patients with oJIA following 72 hour incubation with recombinant *E. coli* hsp dnaJ. Results, expressed as percentage CD3+CD69+ cells, are shown as mean+SD.

FIG. 1C provides an evaluation of the ratio of stimulation index (SI) of PBMC-SFMC paired samples from patients with oJIA stimulated with tetanus toxoid (TT) or recombinant *E. coli* hsp dnaJ (dnaJ) for 96 hours.

FIG. 25A) and production of IFNγ (FIG. 25B) or IL-10 (FIG. 25C) by SFMC of oJIA patients stimulated with non-homologous human peptides 50, 51, 134, 197, 254, 256, 270, 283 and 318 (SEQ ID NOS: 18-26, respectively).

FIGS. 26A to 26E show the results of treatment-induced modulation of T cell responses to dnaJP1. FIG. 26A shows T cell proliferative responses of PBMC stimulated for 5 days with 10 μg/ml of dnaJP1 peptide (SEQ ID NO:3). Evaluation was performed at monthly intervals. Controls included PHA as a general mitogen and dnaJpv (SEQ ID NO:28). Evaluation by FACS at monthly intervals of intracellular cytokine production (pro-inflammatory—FIGS. 26 B, C and D; toleragenic—FIG. 26E) by PBMC of the patients who were responsive at the screening. Results are expressed as % CD3+ cells in dnaJP1 stimulated/unstimulated cultures.

DETAILED DESCRIPTION OF THE INVENTION

Figure 1:
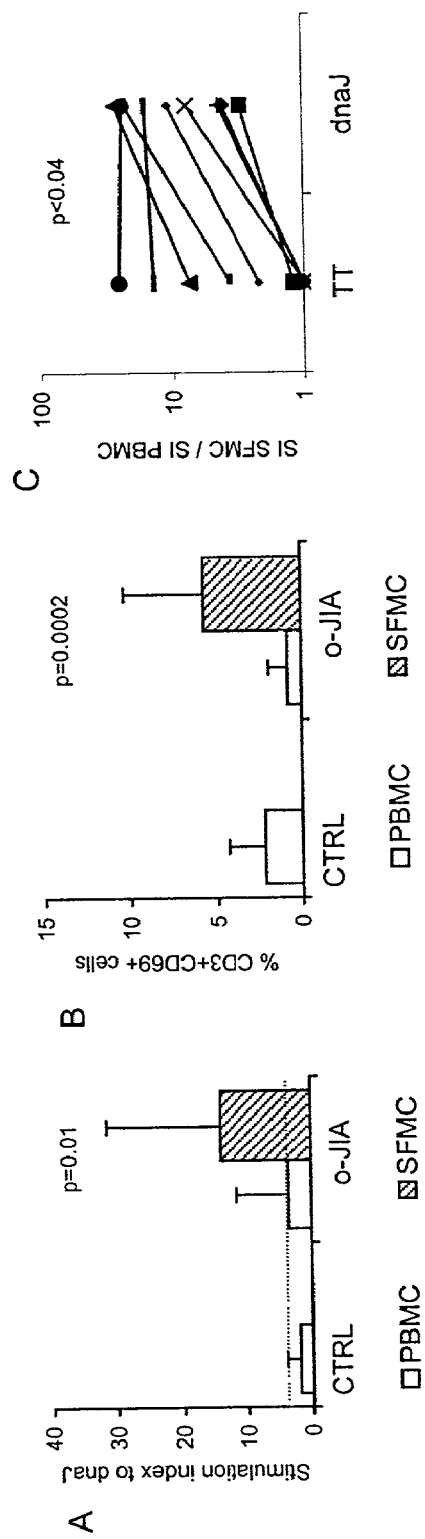
FIGS. 1A to 1C.

The invention provides a method of modulating an immune response in a subject. As disclosed herein, an effective therapeutic strategy for ameliorating the inflammation-related symptoms of an immune-mediated disease, such as arthritis, can be achieved by modulating the underlying immune response, rather than by merely addressing the resulting inflammation. This strategy can be used to regulate the inflammatory response and is applicable to a variety of contexts in which immune modulation is desired, such as mucosal tolerization, DNA vaccination, anergy induction, active immunization, and ex vivo modulation of antigen-specific T cells.

The present invention provides peptides for use in modulating an immune response. Peptides of the invention are immunogenic peptides that are selected for the ability to bind to the most common human HLA class II alleles. As disclosed herein, the immunogenic peptide can be any immunogenic portion of the dnaJ hsp, and generally is a peptide that can bind an MHC class II receptor or a T cell receptor, and that provides an epitope that is substantially specific for a dnaJ polypeptide.

The immunogenic peptides exemplified herein were derived from microbial and mammalian heat shock proteins (hsp), including *E. coli* hsp dnaJ (see GenBank Acc. No. NP_308042 and human dnaJ protein homologs such as HSJ1 (GenBank Acc. No. XP_010863), HDJ1 (GenBank Acc. No. P25685) and HDJ2 GenBank Acc. No. P31689). However, it will be recognized that proteins homologous to *E. coli* dnaJ or the human dnaJ homologs also can be used as a source from which to derive an immunogenic peptide useful in a method of the invention. Such dnaJ homologs are well known in the art and include, for example, those encoded by nucleic acid molecules cloned from various prokaryotic and eukaryotic organisms such as *Yersinia pestis* (GenBank Acc. No. CAC89325), *Saccharomyces cerevisiae* (GenBank Acc. No. NP_013884), zebrafish (GenBank Acc. No. B1846679), chicken (GenBank Acc. No. B1391025), mouse (GenBank Acc. No. NP_064662). It will be recognized that additional dnaJ hsp's from other organisms can be identified and obtained by searching a nucleic acid molecule or protein database such as the National Center for Biotechnology Information (NCBI) nucleotide or protein database using a term such as "dnaJ", "HSJ1", or the like and a search method and search parameters as disclosed herein.

As disclosed herein, peptide portions of the bacterial hsp dnaJ protein and of the human HSJ1, HDJ1 and HDJ2 hsp's, including peptides that are homologous to bacterial hsp dnaJ peptide sequences ("homologous human peptides") and peptides that are not homologous to bacterial hsp dnaJ peptide sequences ("non-homologous human peptides") can modulate the immune response of a subject. Representative bacterial hsp dnaJ peptides and homologous and non-homologous human peptides include:

Bacterial dnaJ Peptides

| dnaJ 4   | QDYYEILGVSKTAEE | (SEQ ID NO:1) |
| dnaJ 22  | RKAYKRLAMKYHPDR | (SEQ ID NO:2) |
| dnaJ 61  | QKRAAYDQYGHAAFEQ | (SEQ ID NO:3) |
| dnaJ 174 | QGFFAVQQTCPHCQG | (SEQ ID NO:4) |
| dnaJ 209 | SKTLSVKIPGAVDTG | (SEQ ID NO:5) |
| dnaJ 242 | GDLYVQVQVKQHPIF | (SEQ ID NO:6) |
| dnaJ 264 | YCEVPTNFAMAALGG | (SEQ ID NO:7) |
| dnaJ 268 | PINFAMAALGGEIEV | (SEQ ID NO:8) |

Homologous Human Peptides

| 2 (HSJI) | ASYYEILDVPRSASA | (homologue of bacterial dnaJ peptide 4; SEQ ID NO:9) |
| 3 (HDJ1) | KDYYQTLGLARGASD | (homologue of bacterial dnaJ peptide 4; SEQ ID NO:10) |
| 5 (HDJ2) | TTYYDVLGVKPNATQ | (homologue of bacterial dnaJ peptide 4; SEQ ID NO:11) |
| 20 (HSJ1) | KKAYRRKALQWHPDK | (homologue of bacterial dnaJ peptide 22; SEQ ID NO:12) |
| 21 (HDJ1) | KRAYRRQALRYHPDK | (homologue of bacterial dnaJ peptide 22; SEQ ID NO:13) |
| 23 (HDJ2) | KKAYRKLALKYHPDK | (homologue of bacterial dnaJ peptide 22; SEQ ID NO:14) |
| 164 (HSJ1) | FRSVSTSTTFVQGRR | (homologue of bacterial dnaJ peptide 174; SEQ ID NO:15) |
| 167 (HDJ2) | PGMVQQIQSVCMECQ | (homologue of bacterial dnaJ peptide 174; SEQ ID NO:16) |
| 176 (HSJ1) | GRRITTRRIMENGQE | (homologue of bacterial dnaJ peptide 174; SEQ ID NO:17) |

Non-Homologous Human Peptides

| 50 (HDJ2) | QAYEVLSDAKKRELYD | (SEQ ID NO:18) |
| 51 (HSJ1) | EAYEVLSDKHKREIYD | (SEQ ID NO:19) |
| 134 (HSJ1) | SGPFFTFSSSFPGHS | (SEQ ID NO:20) |

| | | -continued | | |
|---|---|---|---|---|
| 197 | (HSJ1) | DGQLKSVTINGVPDD | (SEQ ID NO:21) | |
| 254 | (HSJ1) | DLQLAMAYSLSEMEA | (SEQ ID NO:22) | |
| 256 | (HDJ2) | EDLFMCMDIQLVEAL | (SEQ ID NO:23) | |
| 270 | (HDJ2) | LCGFQKPISTLDNRT | (SEQ ID NO:24) | |
| 283 | (HDJ2) | RTIVITSHPGQIVKH | (SEQ ID NO:25) | |
| 318 | (HDJ2) | GRLIIEFKVNFPENG | (SEQ ID NO:26) | |

The immunogenic peptides of the invention include "pro-inflammatory peptides", which result in increased expression of pro-inflammatory cytokines such as interferon-gamma, and "anti-inflammatory peptides", which result in increased expression of anti-inflammatory cytokines such as interleukin-10. The determination as to whether a peptide of the invention has pro-inflammatory activity or anti-inflammatory activity conveniently can be made using in vitro assays as disclosed herein (see Examples 1 and 2), or can be made using any method routinely used in the art for determining, for example, the identity and amounts of cytokines expressed due to contact of the peptide with immunoeffector cells. As used herein, the term "immunoeffector cells" refers to cells that are directly involved in generating or effecting an immune response. Such cells are well known in the art and include B lymphocytes (B cells); antigen presenting cells such as dendritic cells, mononuclear phagocytic cells, macrophages, including Langerhans cells and, in humans, venular endothelial cells (and B cells); and, particularly T cells, for example, T helper cells, T suppressor cells, and cytotoxic T cells.

The immunogenic peptides of the invention can be characterized into two general categories, including those peptides having an amino acid sequence that is relatively conserved among dnaJ hsp's of various species ("homologous peptides"), and those peptide having an amino acid sequence that is not substantially conserved among dnaJ hsp's ("non-homologous peptides"). As used herein, the term "homology" is used to refer to an amino acid sequence or a nucleotide sequence that shares at least about 50% sequence identity with a reference sequence when compared and aligned for maximum correspondence over a comparison window or designated region as measured using any number of sequence comparison algorithms or by manual alignment and visual inspection. For purposes of determining sequence identity, conservative amino acid substitutions such as a substitution of amino acids that have a aliphatic hydrophobic side chain (e.g., alanine, leucine, isoleucine, valine), or of amino acids that have an acid side chain (e.g., aspartic acid, glutamic acid), or of amino acids that have a basic side chain (arginine, lysine), or the like, are considered to be identical. In addition, a determination of homology can allow for one or a few insertions or deletions, preferably one or two insertions or deletions, provided that such insertions or deletions are counted as an amino acid that is not identical for purposes of the comparison. As such, homologous peptides can differ in length by one, two, or a few amino acids, provided the minimum amount of sequence identity is maintained.

As disclosed herein, homologous peptides or polynucleotides of the invention have at least about 50% sequence identity, generally at least about 60% sequence identity, and can have at least about 70% sequence identity or 80% sequence identity or more as compared to a reference peptide or polynucleotide, respectively. For example, bacterial dnaJ peptide 4 (SEQ ID NO:1), which contains 15 amino acids, is homologous to human HSJ1 peptide 2 (SEQ ID NO:9), which contains 15 amino acids, including seven identical amino acids and two conserved substitutions with respect to SEQ ID NO:1 (9/15; 60%); to human HDJ1 peptide 3 (SEQ ID NO:10), which contains 15 amino acids, including six identical amino acids and three conserved substitutions with respect to SEQ ID NO:1 (9/15; 60%); and to human HDJ2 peptide 5 (SEQ ID NO:11), which contains eight identical amino acids with respect to SEQ ID NO:1 (8/15; 53.3%). Non-homologous peptides of the invention include those peptide that are not homologous peptides, but otherwise have the characteristics of an immunogenic peptide of the invention.

The determination of whether a peptide or polynucleotide is homologous for purposes of the present invention can be made by visually comparing two or a few sequences, or can be made using a computer assisted method, which also can be useful for identifying homologous sequences from among a plurality of sequences as can be contained in a protein or nucleic acid molecule database. For example, homology or identity can be measured using sequence analysis software such as the Sequence Analysis Software Package of the Genetics Computer Group (University of Wisconsin Biotechnology Center, 1710 University Avenue, Madison, Wis. 53705). Such software matches similar sequences by assigning degrees of homology to various deletions, substitutions and other modifications. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" is used broadly herein to include reference to a segment of any one of the number of contiguous positions, for example, about 9 to 50 amino acid positions or about 20 to 200 nucleotide position, in which a sequence may be compared to a reference sequence of the same number of contiguous positions after the two sequences are optimally aligned. Methods of alignment of sequence for comparison are well known and include, for example, the local homology algorithm of Smith and Waterman (*Adv. Appl. Math.* 2:482, 1981), the homology alignment algorithm of Needleman and Wunsch (*J. Mol. Biol.* 48:443, 1970), the search for similarity method of Person and Lipman (*Proc. Natl. Acad. Sci., USA* 85:2444, 1988), each of which is incorporated herein by reference; by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals &

Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences.

One example of a useful algorithm is BLAST and BLAST 2.0 algorithms, which are described by Altschul et al. (Nucleic Acids Res. 25:3389-3402, 1977; J. Mol. Biol. 215:403-410, 1990, each of which is incorporated herein by reference). Software for performing BLAST analyses is publicly available through the National Center for Biotechnology Information (available on the world wide web at the URL ncbi.nlm.nih.gov). This algorithm involves first identifying high scoring sequence pairs by identifying short words of length W in the query sequence, which either match or satisfy some positive-valued threshold score T when aligned with a word of the same length in a database sequence. T is referred to as the neighborhood word score threshold (Altschul et al., supra, 1977, 1990). These initial neighborhood word hits act as seeds for initiating searches to find longer high scoring sequence pairs containing them. The word hits are extended in both directions along each sequence for as far as the cumulative alignment score can be increased. Cumulative scores are calculated using, for nucleotide sequences, the parameters M+(reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectations (E) of 10, and the BLOSUM62 scoring matrix (see Henikoff and Henikoff, Proc. Natl. Acad. Sci., USA 89:10915, 1989) alignments (B) of 50, expectation (E) of 10, M=5, N=4, and a comparison of both strands.

The BLAST algorithm also performs a statistical analysis of the similarity between two sequences (see, for example, Karlin and Altschul, Proc. Natl. Acad. Sci., USA 90:5873, 1993, which is incorporated herein by reference). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST"). In particular, five specific BLAST programs are used to perform the following task:
 (1) BLASTP and BLAST3 compare an amino acid query sequence against a protein sequence database;
 (2) BLASTN compares a nucleotide query sequence against a nucleotide sequence database;
 (3) BLASTX compares the six-frame conceptual translation products of a query nucleotide sequence (both strands) against a protein sequence database;
 (4) TBLASTN compares a query protein sequence against a nucleotide sequence database translated in all six reading frames (both strands); and
 (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993, each of which is incorporated herein by reference). Less preferably, the PAM or PAM250 matrices may also be used (Schwartz and Dayhoff, eds., "Matrices for Detecting Distance Relationships: Atlas of Protein Sequence and Structure" (Washington, National Biomedical Research Foundation 1978)). BLAST programs are accessible through the U.S. National Library of Medicine, for example, on the world wide web at the URL ncbi.nlm.nih.gov. The parameters used with the above algorithms may be adapted depending on the sequence length and degree of homology studied. In some embodiments, the parameters may be the default parameters used by the algorithms in the absence of instructions from the user. Such search methods also can be used to identify dnaJ hsp's from a database.

A peptide of the invention can be prepared using methods of chemical peptide synthesis, can be expressed from an encoding polynucleotide, or isolated following cleavage of a dnaJ hsp. Techniques for purifying, synthesizing or producing peptides in recombinant form are convenient and well known in the art, and are suitable for producing immunogenic peptides of sufficient purity for use in a method of the invention. In this respect, the term "isolated" or "substantially pure" denotes a polypeptide or polynucleotide that is substantially free of other compounds with which it may normally be associated in vivo. In the context of a method of the invention, the term substantially pure refers to substantially homogenous peptides or polynucleotides, where homogeneity is determined by reference to purity standards known in the art such as purity sufficient to allow the N-terminal amino acid sequence of the protein to be obtained. Preferably, the peptide or polynucleotide is sufficiently isolated such that it can be used for administration to a subject. As such, an isolated peptide or polypeptide generally constitutes at least about 50% of a sample containing the peptide, usually at least about 75%, particularly at least about 90%, and preferably about 95% to 99% or more. It should be recognized that such a measure of purity refers to the peptide alone, or as a starting material, for example, for formulation into a composition, in which case the isolated peptide of the invention can comprise a component of the composition, which can further contain additional components as disclosed herein, including additional isolated peptides of the invention.

Substantially pure dnaJ proteins and peptides can be obtained from intact microorganisms, particularly bacteria, through microbial expression, by chemical or biological synthesis, or using routine purification methods known in the art, including, for example, affinity chromatography. Such techniques can be utilized to obtain immunogenic peptide fragments of a dnaJ hsp. For example, proteins or peptides useful to prepare a vaccine composition of the invention can be chemically synthesized using methods that involve t-BOC or FMOC protection of alpha-amino groups. Both methods involve stepwise synthesis, whereby a single amino acid is added at each step starting from the C-terminus of the peptide (see, for example, Coligan et al., Current Protocols in Immunology, Wiley Interscience, 1991, Unit 9). Peptides of the invention can also be synthesized by various well known solid phase peptide synthesis methods (see, for example, Merrifield, J. Am. Chem. Soc., 85:2149, 1962; Stewart and Young, Solid Phase Peptides Synthesis (Freeman, San Francisco, 1969) see pages 27-62) using, for example, a copoly(styrene-divinylbenzene) containing about 0.1-1.0 mmol amines/g polymer. On completion of chemical synthesis, the peptides can be deprotected and cleaved from the polymer by treatment with liquid HF-10% anisole for about 15 minutes to 1 hour at 0° C.

After evaporation of the reagents, the peptides are extracted from the polymer with 1% acetic acid solution, which is then lyophilized to yield the crude material, which can be purified using a method such as gel filtration chromatography, for example, on a SEPHADEX.RTM G-15 affinity column or a SEPHAROSE.RTM affinity column using 5% acetic acid as a solvent. Lyophilization of appropriate fractions of the column yield substantially homogeneous peptide or peptide derivatives, which can be characterized by standard techniques such as amino acid analysis, thin layer chromatography, high performance liquid chromatography, ultraviolet absorption spectroscopy, molar rotation, or solubility, and can be sequenced, for example, by the solid phase Edman degradation method.

If desired, an immunogenic peptide of the invention can be modified, for example, to increase the ability of the peptide to act as an immunogen or a toleragen, to increase the stability of the peptide in a subject or other medium, or for any other purpose as desired. For example, the peptide can be modified by glycosylation, which can be effected by linking a carbohydrate moiety to a reactive side chain of an amino acid of the peptide or by including one or a few additional amino acids at the N-terminus or C-terminus of the peptide and linking the carbohydrate moiety to the additional amino acid. The linkage can be any linkage commonly found in a glycoprotein, for example, an N-linked or O-linked carbohydrate to an asparagine residue or a serine residue, respectively, or can be any other linkage that conveniently can be effected.

An immunogenic peptide of the invention also can be modified by being operatively linked to one or more other peptides or polypeptides. As such, the present invention also provides a chimeric polypeptide, which includes a peptide of the invention operatively linked to at least one heterologous polypeptide. As used herein, the term "operatively linked" means that two or more peptides (or two or more polynucleotides) are joined together such that the functions of the linked peptides (or polynucleotides) is maintained, and such that the chimeric polypeptide (or recombinant nucleic acid molecule) exhibits the functions of each component peptide (or polynucleotide). For example, a chimeric polypeptide of the invention can include a peptide of the invention operatively linked to a peptide tag such as a polyhistidine tag, such that the peptide can be identified in a sample or isolated from a mixture using a nickel chelate reagent. A peptide of the invention also can be linked, for example, a cell compartmentalization domain, which can facilitate localization of the peptide compartment of a cell, for example, a peptide that is expressed following administration of a recombinant nucleic acid molecule encoding the chimeric polypeptide to a subject. The cell compartmentalization domain can facilitate localization of the peptide to the cytosol, nucleus, plasma membrane, endoplasmic reticulum, medial trans-Golgi cistemae, or a lysosome or endosome; or can be a membrane translocating peptide, which can facilitate transport of immunogenic peptide across a cell membrane; or a secretory peptide, which can facilitate secretion of the peptide out of a cell (see, for example, Hancock et al., EMBO J. 10:4033-4039, 1991; Buss et al., Mol. Cell. Biol. 8:3960-3963, 1988; U.S. Pat. No. 5,776,689, each of which is incorporated herein by reference).

The present invention also provides a polynucleotide encoding an immunogenic peptide of the invention. The polynucleotide can be single stranded or double stranded, and can be a ribonucleic acid molecule (RNA), a deoxyribonucleic acid molecule (DNA), or a hybrid thereof. In addition, the invention provides a recombinant nucleic acid molecule, which includes a polynucleotide of the invention operatively linked to at least one heterologous nucleotide sequence. The heterologous nucleotide sequence can be any nucleotide sequence that is not normally found in contiguous linkage with the polynucleotide of the invention in nature. For example, the heterologous nucleotide sequence can be an expression control sequence such as a transcription regulatory element or a translation regulatory element, or a combination thereof; or can encode a polypeptide such as a cytokine or other immunomodulatory agent, a peptide tag, a cellular localization domain, or the like. Where the recombinant nucleic acid molecule encodes a peptide of the invention and a second (or more) functional polypeptide such as one or more additional peptides of the invention or one or more cytokines or the like, the recombinant nucleic acid molecule can further encode a protease recognition site between each of the encoded peptides such that, upon expression, each of the encoded peptides is released in a form that is free from the other encoded peptides or polypeptides.

The present invention also provided is a vector containing a polynucleotide of the invention, and further provides a cell that contain a polynucleotide or vector of the invention. The vector can be a cloning vector, which can be useful for producing a large amount of polynucleotide or recombinant nucleic acid molecule of the invention contained therein, or can be an expression vector, which can be useful if the polynucleotide is to be administered to a cell or subject for the purpose of expressing the encoded peptide. Such vectors are well known in the art and include, for example, plasmid vectors and viral vectors, including vectors derived from a retrovirus, adenovirus, adeno-associated virus, vaccinia virus or the like.

A commonly used plasmid vector which operatively encodes foreign structural gene inserts is the pBR322 plasmid. pBR322 includes a gene for conferring ampicillin resistance as a marker; however, for use in humans, such ampicillin resistance should be avoided. Modified vectors which are useful in gene immunization protocols but do not confer ampicillin resistance are described, for example, in U.S. Ser. No. 08/593,554, filed Jan. 30, 1996 which is incorporated herein by reference.

Various viral vectors that can be utilized in the invention include adenovirus, herpes virus, vaccinia, or an RNA virus such as a retrovirus. Preferably, the retroviral vector is a derivative of a murine or avian retrovirus. Examples of retroviral vectors in which a single foreign gene can be inserted include, but are not limited to Moloney murine leukemia virus (MoMuLV), Harvey murine sarcoma virus (HaMuS-V), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, ψ2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

Certain advantages can be obtained by administering polynucleotide encoding a peptide of the invention as a vaccine" in lieu of administering the peptide as a traditional vaccine, including, for example, that the risk of potential toxicity such as anaphylactic shock associated with a proteinaceous vaccine is substantially avoided. Where contacted with a cell or administered to a subject, the polynucleotide or recombinant nucleic acid molecule of the invention, or vector containing the polynucleotide, can be administered as a "naked" DNA, or can be formulated into a delivery vehicle such as a liposome or colloidal particles, which can facilitate uptake of the polynucleotide and can reduce the likelihood of degradation of the polynucleotide prior to uptake by a cell.

The present invention also provide a composition, which contains at least one peptide of the invention and can provide a plurality of different immunogenic peptides of the invention, for example, a composition containing any of the peptides set forth as SEQ ID NOS:1-26, or a composition containing any combination of such peptides, particularly a composition containing a combination of pro-inflammatory peptides, and a composition containing a combination of anti-inflammatory peptides. A composition of the invention generally is formulated in a physiologically acceptable solution and, if desired, can further contain one or more immunoadjuvants, for example, one or more cytokines, Freund's complete adjuvant, Freund's incomplete adjuvant, alum, or the like. Generally, where the composition contains one or more cytokines, the cytokines have an activity that is the same as or complements the inflammatory activity of the peptide of the invention. The composition also can contain any immunoadjuvant, including an immunostimulant or, if desired, an immunosuppressant, which can modulate the systemic immune response of an individual. Suitable substances having this activity are well known in the art and include IL-6, which can stimulate suppressor or cytotoxic T cells, and cyclosporin A and anti-CD4 antibodies, which can suppress the immune response. Such compounds can be administered separately or as a mixture with a vaccine of the invention.

The term "cytokine" is used broadly herein to refer to soluble glycoproteins that are released by cells of the immune system and act non-enzymatically through specific receptors to regulate immune responses. As such, the term "cytokine" as used herein includes chemokines, interleukins, lymphokines, monokines, interferons, colony stimulating factors, platelet activating factors, tumor necrosis factor-alpha, and receptor associated proteins, as well as functional fragments thereof. As used herein, the term "functional fragment" refers to a peptide or polypeptide portion of a protein that possesses the biological function or activity characteristic of the native protein. For example, a functional fragment of an IL-10 or IL-4 has, for example, substantially the same anti-inflammatory activity as naturally occurring or recombinantly produced IL-10 or IL-4, respectively, whereas a functional fragment of IFNγ or TNFα has, for example, substantially the same pro-inflammatory activity as naturally occurring or recombinantly produced IFNγ or TNFα, respectively.

Cytokines are well known in the art and include, for example, endothelial monocyte activating polypeptide II (EMAP-II), granulocyte-macrophage colony stimulating factor (GM-CSF), granulocyte-CSF (G-CSF), macrophage-CSF (M-CSF), IL-1, IL-2, IL-3, IL-4, IL-5, IL-6, IL-10, IL-12, IL-13, etc., the interferons, including IFNα, IFNβ, and IFNγ, and TNF-α, each of which is associated with a particular biologic, morphologic, or phenotypic alteration in a cell or cell mechanism. The chemokines are further exemplified by the members of the CXC chemokine (or α) subfamily, which possess an intervening amino acid between the first two conserved cysteines; the members of the CC (or β) subfamily, which do not contain such an intervening amino acid residue; and the C (or γ) chemokines, which lack the first and third cysteine residues. In general, the α chemokine members are active on neutrophils and T lymphocytes (T cells), and the β chemokines are active on monocytes, macrophages and T cells. Several members of the α and β chemokine sub-families also are active on dendritic cells, which are migratory cells that exhibit potent antigen-presenting properties and are thought to participate in the pathophysiology of many inflammatory diseases (Xu et al., J. Leuk. Biol., 60:365-71, 1996; and Sozzani et al., J. Immunol., 159:1993-2000, 1997). A fourth human CX3C-type chemokine, fractalkine, also has been described (Bazan et al., Nature, 385:640-4, 1997; Imai et al., Cell, 91:521-30, 1997; Mackay, Curr. Biol. 7:R384-6, 1997). Unlike other chemokines, fractalkine exists in membrane and soluble forms. The soluble form is a potent chemoattractant for monocytes and T cells. The cell surface receptor for this chemokine is termed CX3CR1.

The α chemokines (also known as IL-8) are exemplified by granulocyte chemotactic protein-2 (GCP-2); growth-related oncogene-α (GRO-α) GRO-β, and GRO-γ; epithelial cell-derived neutrophil activating peptide-78 (ENA-78); platelet basic protein (PBP); connective tissue activating peptide III (CTAP III); neutrophil activating peptide-2 (NAP-2); low affinity platelet factor-4 (LAPF-4); monokine induced by IFNγ (MIG); platelet factor 4 (PF4); interferon inducible protein 10 (IP-10); the stromal cell derived factors SDF-1α, SDF-1β, and SDF-2. The βchemokines are exemplified by the monocyte chemotactic proteins MCP-1, MCP-2, MCP-3, MCP-4, and MCP-5; the macrophage inhibitory proteins MIP-1α, MIP-1β, MIP-1γ, MIP-2, MIP-2α, MIP- 2β, MIP-3α, MIP-3β, MIP-4, and MIP-5; macrophage-derived chemokine (MDC); human chemokine 1 (HCC-1); LD78β; RANTES; eotaxin 1; eotaxin 2; TARC; SCYA17 and I-309; dendritic cell chemokine-1 (DC-CK-1). The γ chemokines are exemplified by lymphotactin.

A composition of the invention can be prepared for administration to a subject by mixing the immunogenic peptide or peptides with physiologically acceptable carriers. Such carriers will be nontoxic to recipients at the dosages and concentrations employed. Ordinarily, the preparation of such compositions entails combining the particular vaccine antigen with saline, buffers, antioxidants such as ascorbic acid, low molecular weight (less than about 10 residues) polypeptides, proteins, amino acids, carbohydrates including glucose or dextrans, or chelating agents such as EDTA, glutathione and other stabilizers and excipients. Such compositions can be in suspension, emulsion or lyophilized form and are formulated under conditions such that they are suitably prepared and approved for use in the desired application.

A physiologically acceptable carrier can be any material that, when combined with an immunogenic peptide or a polynucleotide of the invention, allows the ingredient to retain biological activity and does not undesirably disrupt a reaction with the subject's immune system. Examples include, but are not limited to, any of the standard physiologically acceptable carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Co., Easton Pa. 18042, USA).

For administration to a subject, a peptide, or an encoding polynucleotide, generally is formulated as a composition. Accordingly, the present invention provides a composition, which generally contains, in addition to the peptide or polynucleotide of the invention, a carrier into which the peptide or polynucleotide can be conveniently formulated for administration. For example, the carrier can be an aqueous solution such as physiologically buffered saline or other solvent or vehicle such as a glycol, glycerol, an oil such as olive oil or an injectable organic esters. A carrier also can include a physiologically acceptable compound that acts, for example, to stabilize the peptide or encoding polynucleotide or to increase its absorption. Physiologically acceptable compounds include, for example, carbohydrates, such as glucose, sucrose or dextrans, antioxidants, such as ascorbic acid or glutathione, chelating agents, low molecular weight proteins or other stabilizers or excipients. Similarly, a cell that has been treated in culture for purposes of the practicing the methods of the invention, for example, synovial fluid mononuclear cells, dendritic cells, or the like, also can be formulated in a composition when the cells are to be administered to a subject.

It will be recognized to the skilled clinician choice of a carrier, including a physiologically acceptable compound, depends, for example, on the manner in which the peptide or encoding polynucleotide is to be administered, as well as on the route of administration of the composition. Where the composition is administered under immunizing conditions, i.e., as a vaccine, it generally is administered intramuscularly, intradermally, or subcutaneously, but also can be administered parenterally such as intravenously, and can be administered by injection, intubation, or other such method known in the art. Where the desired modulation of the immune system is tolerization, the composition preferably is administered orally, or can be administered as above.

A composition of the invention also can contain a second reagent such as a diagnostic reagent, nutritional substance, toxin, or therapeutic agent, for example, a cancer chemotherapeutic agent. Preferably, the second reagent is an immunomodulatory agent, for example, an immunostimulatory agent such as a cytokine or a B7 molecule. In addition, where it is desired to stimulate an immune response, the composition can contain an adjuvant, for example, alum, DETOX adjuvant (Ribi Immunochem Research, Inc.; Hamilton Mont.), or Freund's complete or incomplete adjuvant. The addition of an adjuvant can enhance the immunogenicity of a peptide of the invention, thus decreasing the amount of antigen required to stimulate an immune response. Adjuvants can augment the immune response by prolonging antigen persistence, enhancing co-stimulatory signals, inducing granuloma formation, stimulating lymphocyte proliferation nonspecifically, or improving apposition of a T cell and an APC.

A composition comprising a peptide or polynucleotide of the invention also can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77, 1981, each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating material. Cationic liposomes, for example, also can be modified with specific receptors or ligands (Morishita et al., *J. Clin. Invest.*, 91:2580-2585, 1993, which is incorporated herein by reference). In addition, a polynucleotide agent can be introduced into a cell using, for example, adenovirus-polylysine DNA complexes (see, for example, Michael et al., *J. Biol. Chem.* 268:6866-6869, 1993, which is incorporated herein by reference).

Accordingly, the present invention provides a method of modulating an immune response in a subject by administering an immunogenic peptide portion of a dnaJ hsp or a polynucleotide encoding such a peptide to the subject. As disclosed herein the dnaJ hsp can be a prokaryotic or eukaryotic dnaJ hsp, including, for example, a bacterial dnaJ hsp such as an *E. coli* dnaJ hsp; an invertebrate dnaJ hsp such as a yeast dnaJ hsp; or a vertebrate dnaJ hsp such as a mammalian dnaJ hsp, including a human dnaJ hsp such as human HSJ1, HDJ1 or HDJ2.

A method of the invention can modulate an immune response by increasing an inflammatory response associated with the immune response or by decreasing an inflammatory response associated with the immune response. Thus, in one embodiment, a method of the invention provides a means for augmenting or inducing an inflammatory response in the subject. Such a method can be performed by administering a peptide having pro-inflammatory activity, i.e., a pro-inflammatory peptide, to the subject under immunizing conditions; by administering an anti-inflammatory peptide to the subject under tolerizing conditions; or by administering a combination of such peptides, for example, by administering two or more pro-inflammatory peptides under immunizing conditions, or two or more anti-inflammatory peptides under tolerizing conditions, or at least one pro-inflammatory peptide under immunizing conditions and at least one anti-inflammatory peptide under tolerizing conditions. A method of augmenting or inducing an inflammatory response can result in an increase in the level of a pro-inflammatory cytokine such as IFNγ, TNFα, IL-1, IL-6, IL-12, or IL-23, in the subject, or a decrease in the level of an anti-inflammatory cytokine such as IL-4, IL-10, or TGFβ, in the subject, or combinations thereof.

A method of the invention also provides a means for reducing or inhibiting an inflammatory response in the subject by administering a peptide having anti-inflammatory activity to the subject under immunizing conditions; or by administering a pro-inflammatory peptide to the subject under tolerizing conditions; or by administering a combination of such peptides, for example, for example, by administering two or more pro-inflammatory peptides under tolerizing conditions, or two or more anti-inflammatory peptides under immunizing conditions, or at least one pro-inflammatory peptides under tolerizing conditions and at least one anti-inflammatory peptide under immunizing conditions. Such a method can result in an increase in the level of an anti-inflammatory cytokine such as IL-4, IL-10, or TGFβ in the subject, or a decrease in the level of a pro-inflammatory cytokine such as IFNγ, TNFα, IL-1, IL-6, IL-12, or IL-23, in the subject, or combinations thereof.

As disclosed herein, one or a combination of immunogenic peptide portions of a dnaJ hsp can be administered, including, for example, any one or any combination of the immunogenic peptides exemplified by SEQ ID NOS:1-26. The skilled clinician will recognize in view of the present disclosure that a peptide of the invention is administered to a subject under immunizing conditions or under tolerizing conditions, depending on whether the peptide is a pro-inflammatory peptide or an anti-inflammatory peptide, and whether the peptide is being administered to augment or induce an inflammatory response or to reduce or inhibit an inflammatory response.

As used herein, the term "under immunizing conditions" means that a peptide of the invention is contacted with a cell or administered to a subject such that it can effect its immunogenic activity. As such, the peptide, which is a T cell immunogen, generally will be administered in an immunogenic amount, typically as a priming dose followed some time later by one or more booster doses, intradermally, subcutaneously, or intramuscularly, and, if desired, formulated in a composition that includes an immunoadjuvant such as Freund's complete or incomplete adjuvant. As used herein, the term "under tolerizing conditions" means that a peptide of the invention is contacted with a cell or administered to a subject such that it induces tolerization to the otherwise immunogenic activity. As a result, a subject, for example, is tolerized to the peptide such that it is recognized a "self" by the subject and cannot effect an immune response. A peptide can be administered under tolerizing conditions by administering a tolerizing amount of the peptide, generally a small amount over a period of time, intradermally, subcutaneously, intramuscularly, or, preferably, mucosally, for example, via nasal spray or by eating.

A method of the invention can be practiced with respect to a subject having, or predisposed or susceptible to, any condition in which it is desired to modulate an immune response, including a subject that has an immunologic disorder, or is susceptible or predisposed to an immunological disorder. The subject generally is a vertebrate subject, and particularly a mammal, including a domesticated animal such as a cat, a dog, or a horse; a farm animal such as an ovine, bovine or porcine animal; or a human. The immunological disorder can be a disorder of the immune system such as an autoimmune disease, for example, an arthritis such as oligoarticular juvenile idiopathic arthritis (oJIA), or an immunodeficiency disease such as acquired immunodeficiency disease (AIDS). Additional conditions in which it can be desired to modulate the immune response include conditions in which the subject has not developed a sufficient immune response, for example, in response to an infectious disease or a cancer, or a condition in which the subject has too great of an immune response, for example, a subject suffering from an inflammatory bowel disease other than an auto-immune disease or a subject suffering from bacterial sepsis.

The total amount of a composition to be administered in practicing a method of the invention can be administered to a subject as a single dose, either as a bolus or by infusion over a relatively short period of time, and can be followed up with one or more booster doses over a period of time. The amount of the composition to stimulate an immune response in a subject depends on various factors including the age and general health of the subject, as well as the route of administration and the number of treatments to be administered. In view of these factors, the skilled clinician will know to adjust the particular dosage as necessary. In general, the formulation of the composition and the routes and frequency of administration are determined, initially, using Phase I (see Example 8) and Phase II clinical trials.

An immunogenic peptide of the invention preferably is administered in a manner sufficient to selectively stimulate IgA production in the gastrointestinal tract of the subject and induce oral tolerance. Methods of inducing oral tolerance by feeding an antigen to a human or animal subject are well known (see, for example, Husby et al., J. Immunol. 152: 4663-4670 (1994), which is incorporated herein by reference). Thus, where tolerization is desired, the peptides of the invention can be administered concomitantly with an IgA immunostimulant, which induces IgM switching to IgA; for example, TGF-β, which can also inhibit systemic helper T cell activity. Preferably, the immunogenic peptide and, when present, IgA immunostimulant, is administered enterally to localize the effect of the vaccine in the gastrointestinal tract. However, the peptides of the invention can be administered in any other manner accepted in the immunotherapeutic art, for example, intravascularly, intradermally, subcutaneously, intramuscularly, or intraperitoneally.

A polynucleotide can be administered by any route commonly used for an immunological procedure, particularly intradermally (see, for example, U.S. Ser. No. 08/446,691, filed Jun. 7, 1995, which is incorporated herein by reference; see, also, U.S. Ser. No. 08/593,554). According to these disclosures, recombinant gene expression vectors are administered by means such as injection, absorption or transdermal transmission across the skin or mucosa of the host.

The protocol for administration of a peptide or polynucleotide of the invention will vary with their composition as well as the age, weight and condition of the patient. However, a preferred protocol for administration of a peptide involves daily oral (enteral) administration of immunologically effective dosages of the vaccine, with or without other forms of therapy, as described above, or conventional anti-inflammatory treatments (e.g., use of steroidal or nonsteroidal anti-inflammatory medicaments and/or analgesics). Depending on the frequency of dosage, an immunologically effective dosage of each peptide vaccine of the invention will range from about 10 μg to 100 mg, generally about 100 μg to 100 mg, usually about 1 mg to 50 mg, and particularly about 25 mg of antigenic protein or peptide. Daily dosages of antigenic peptide will generally be administered in amounts of about 1 mg/day.

The dosage of a polynucleotide to be administered according to a method of the invention will vary depending on the desired response by the host and the levels of gene expression achievable by the vector used. Generally, for introduction of a naked polynucleotide by an intradermal route, up to about 100 µg to 200 µg of the polynucleotide can be administered in a single dosage, although as little as about 0.3 µg of polynucleotide administered through skin or mucosa can induce long lasting immune responses. For purposes of the invention, however, it is sufficient that the naked gene expression vectors be supplied at a dosage sufficient to cause expression of the encoded immunogenic peptide. These dosages can be modified to achieve differing levels of expression, thus providing an immunizing amount or a tolerizing amount. Means to confirm the presence and quantity of expressed peptides are well known in the art and include, for example, immunoassays such as enzyme-linked immunosorbent assays, PCR techniques, and immunohistological analyses. Dosages of the administered polynucleotides can be adjusted to achieve the desired level of expression based on information provided by these detection and quantification means as well as in vivo clinical signs known to practitioners in the clinical arts.

Conventional dosages of an immunostimulant or immunosuppressant can be included in a composition with the peptide or polynucleotide of the invention, or can be administered separately prior to, at the time of, or after administration of the peptide, for example, about 1 µg/kg to 100 µg/kg IL-6. Such dosages will be based on information that is known in the art or otherwise readily ascertainable using commonly practiced methods. Treatment of early stage patients can be continued to, through, or beyond observation of the surrogate end-point.

Administration of a peptide or polynucleotide of the invention to a subject predisposed to, but not yet having developed, the disease can be accomplished by short term administration of one or more dosages of the composition sufficient to produce detectable increases, for example, of anti-dnaJ peptide IgA in a fluid in the gastrointestinal tract or peripheral vascular circulation of the patient. Generally, the preferred use of the vaccines of the invention is in a patient with early stage disease.

The efficacy of a therapeutic method of the invention over time can be identified by an absence of symptoms or clinical signs of an immunological disorder in a subject predisposed to the disorder, but not yet exhibiting the signs or symptoms of the disorder at the time of onset of therapy. In patients diagnosed as having the immunological disorder, or other condition in which it is desirable to modulate the immune response, the efficacy of a method of the invention can be evaluated by measuring a lessening in the severity of the signs or symptoms in the subject or by the occurrence of a surrogate end-point for the disorder.

With respect to an immunological disorder such as an autoimmune arthritis, conventional parameters for clinical signs and symptoms of arthritis and surrogate end-points for the disease are well known in the art and include, for example, performing "Ritchie Index" measurements for joint tenderness (Ritchie et al., Quart. J. Med., 37:393-406 (1968)), measuring the number of swollen joints, the daily duration of morning joint stiffness, grip strength, or intensity of pain on a visual analogue scale (Huskisson, Lancet, 2:1127-1131 (1974)), and measuring relative levels of use of an anti-inflammatory agent or analgesic by the patient. Additional conventional clinical parameters that can be followed include, for example, disease duration, erythrocyte sedimentation rate (ESR), C-reactive protein (CRP) levels, number of active joints (NAA), severity of articular index (CSA), remission interval, Children's Health Assessment Questionnaire (CHAQ), and response to treatment with dnaJ peptide (characterization of responders vs. non-responders).

Based on the results of double-blind clinical trials of an *E. coli* extract (Brackertz et al., J. Rheum. 16:19-23, 1989), few if any adverse side effects in the subject are expected due to administration of a composition of the invention. For example, gastrointestinal irritation can occur, but would be expected to be low. Toxicity of these compositions can be monitored by conventional means, such as periodic laboratory evaluations through assays of such variables as hematocrit, hemoglobin, thrombocyte and rheumatoid factor levels as well as blood chemistry. For other immunological disorder or other conditions in which it desired to modulate the immune response of a subject, the signs and symptoms characteristic of the disorder will be monitored.

The present invention also provides a method of modulating immunoeffector cell responsiveness. Such a method can be performed, for example, by contacting immunoeffector cells with a peptide portion of a dnaJ hsp or with a polynucleotide encoding such a peptide. The dnaJ hsp from which the peptide is derived can be any dnaJ hsp as disclosed herein or otherwise known in the art, and can, but need not, be formulated in a composition, which also can contain, if desired, an immunoadjuvant or other immunomodulatory agent, for example, one or more cytokines. The immunoeffector cells, which can be any cells involved in a T cell mediated immune response, including antigen presenting cells such as dendritic cells and, in particular, T cells, can be contacted with the peptide in vivo by administering the peptide to a subject, or can be contacted in vitro.

Where immunoeffector cells are contacted in vitro (or ex vivo), the method can further include administering the contacted immunoeffector cells to a subject, thus providing a means to modulate an immune response in the subject. The immunoeffector cells can be autologous cells that have been removed from the patient, contacted with the peptide ex vivo, then administered back into the subject. Such a method provides the advantage that the immunoeffector cells can be allowed to proliferate in vitro, if desired, then the expanded population of cells can be administered to the subject. The immunoeffector cells also can be allogeneic with respect to the subject, for example, cells selected from an individual that is related to the subject and shares common haplotypes with the subject, or cells selected from a population of cell lines for which the haplotypes are known and are at least partially haplotype matched to the subject. Such cells, upon administration to the subject, can modulate the immune response in the subject by augmenting or inducing an inflammatory response in the subject, or by reducing or inhibiting an inflammatory response in the subject.

The following examples are intended to illustrate but not limit the invention.

EXAMPLE 1

Cellular Immune Responce to Recombinant *E. coli* dnaJ

Proliferative responses to recombinant *E. coli* hsp dnaJ (dnaJ) of peripheral blood mononuclear cells (PBMC) from 10 healthy subjects ("control") and 21 patients with oligoarticular juvenile idiopathic arthritis ("oJIA") were not significantly different (FIG. 1A). To evaluate whether dnaJ-specific T cells were enriched at the synovial sites of inflammation, synovial fluid mononuclear cells (SFMC) from all patients with oJIA were stimulated with dnaJ for 96 hr. The mean stimulation index (SI) of SFMC was significantly higher than the SI of the corresponding PBMC (p=0.01; FIG. 1A). In addition, following stimulation with dnaJ, the percentage of activated T cells, evaluated as CD3+CD69+ cells, was significantly higher (p=0.0002) in SFMC with respect to PBMC (FIG. 1B).

To confirm that the increased response of SFMC to dnaJ was not secondary to a non-specific increase in SFMC reactivity, the proliferative responses of cells from both compartments to an unrelated memory antigen, tetanus toxoid (TT). The proliferative response to TT tended to be higher in SFMC (median SI=6.0) as compared to PBMC (median SI=12.3). In order to compare the differences in the responses of PBMC and SFMC to dnaJ and TT, the ratio of the stimulation index obtained in the two compartments for each of the two antigens was calculated. As shown in FIG. 1C, the ratio SI SFMC/SI PBMC was significantly (p=0.038) higher following stimulation with dnaJ than with TT.

Figure 2:
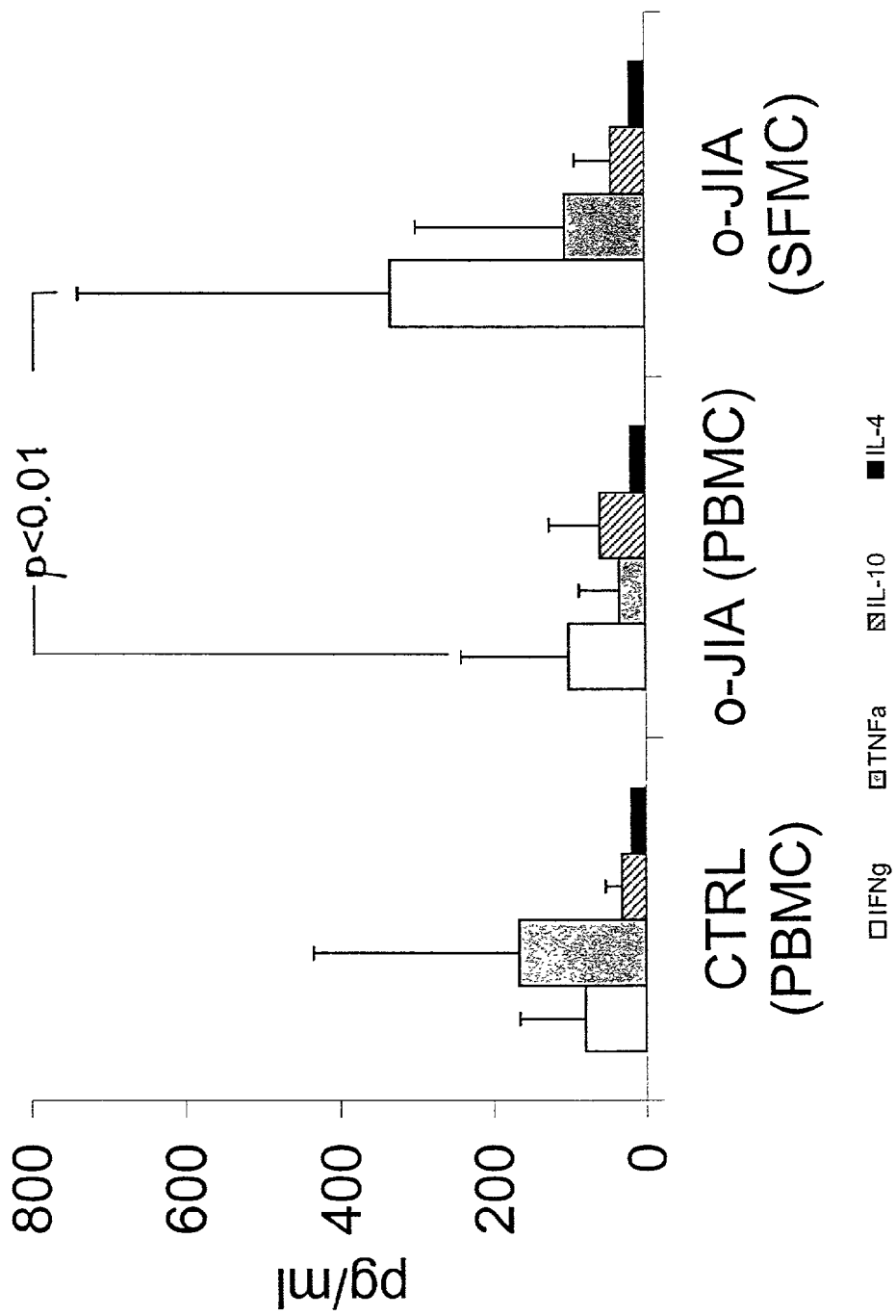
FIG. 2 shows cytokine production (IFNγ, TNFα, IL-10, and IL-4, as indicated) in culture supernatants of PBMC or SFMC from healthy subjects (CTRL) or patients with oJIA stimulated with recombinant *E. coli* hsp dnaJ for 72 hours. Results, expressed as pg/ml, are shown as mean+SD.

The production of the pro-inflammatory cytokines interferon-gamma (IFNγ) and tumor necrosis factor-alpha (TNFα), and the anti-inflammatory cytokines interleukin-4 (IL-4) and IL-10 was evaluated in culture supernatants of PBMC from healthy controls and in PBMC-SFMC paired samples from patients with oJIA incubated for 72 hr with or without dnaJ. As shown in FIG. 2, there was no difference in cytokine production from PBMC of patients and controls. Analysis of PBMC-SFMC paired samples for cytokine production revealed that stimulation with dnaJ induced a significantly higher production (p<0.01) of IFNγ in SFMC than in PBMC from patients with oJIA; IFNγ) production was significantly inversely correlated to disease duration (R=−0.40, p=0.034). TNFα and IL-10 production were comparable in the two compartments. IL-4 levels were below the detection limit in both controls and patients, in supernatants from PBMC and SFMC.

Table 1 shows the results of an evaluation of the production of pro-inflammatory and anti-inflammatory cytokines in culture supernatant of SFMC from patients with oJIA, incubated with the recombinant E. coli dnaJ protein for 72 hr, then restimulated with autologous irradiated feeder cells in presence or absence of an unrelated control peptide, ovalbumin (OVA), or the E. coli hsp dnaJ derived peptides for 72 hr. Results are expressed as pg/ml (mean+SD).

TABLE 1

Pro-inflammatory and anti-inflammatory cytokine production

| Peptide | IFNγ | TNFα | IL-6 | IL-10 | IL-4 |
|---|---|---|---|---|---|
| 4 | 38.5 ± 47.7 | 9.8 ± 21.2 | 49.8 ± 54.0 | 5.4 ± 6.9 | <0.39 |
| 22 | 27 ± 38.0 | 14.1 ± 26.8 | 45.7 ± 57.7 | 4.4 ± 2.7 | <0.39 |
| 61 | 31 ± 45.7 | 22.6 ± 35.3 | 47.6 ± 70.5 | <3.9 | <0.39 |
| 174 | 29.8 ± 44.6 | 16.1 ± 31.5 | 47.3 ± 61.2 | 4.2 ± 1.9 | <0.39 |
| 209 | 41.3 ± 46.9 | 15.3 ± 29.2 | 56.6 ± 65.9 | 6.2 ± 5.8 | <0.39 |
| 242 | 41.2 ± 48.8 | 14.2 ± 29.2 | 34.1 ± 41.7 | 5.3 ± 6.6 | <0.39 |
| 264 | 44.9 ± 55.8 | 14.0 ± 29.3 | 47.4 ± 61.2 | <3.9 | <0.39 |
| 268 | 34.7 ± 51.2 | 17.2 ± 30.1 | 45 ± 58.4 | <3.9 | <0.39 |

These results demonstrate that the proliferative response and IFNγ production to dnaJ are higher in the synovial compartment than in the peripheral blood of patients oJIA, and indicate that E. coli hsp dnaJ or a homologous protein or peptide portion thereof can have a role in joints inflammatory process.

EXAMPLE 2

Cellular Immune Responce to Synthetic Peptides Derived from Recombinant E. coli dnaJ In order to identify possible relevant epitopes on the bacterial dnaJ protein, PBMC and SFMC of patients with oJIA were incubated for 72 hr with dnaJ, and restimulated with autologous feeder cells the in presence or absence of selected E. coli derived MHC class II binder peptides for 96 hr. A total of 8 peptides were tested, including three peptides (pep4, pep22, pep174) that are derived from the N-terminal region of E. coli dnaJ and present sequence homologies to each of the three human dnaJ isoforms (HDJ1, HDJ2, HSJ1; homologous peptides), and five peptides that are derived from the C-terminal region of E. coli dnaJ and do not present any homology with the human counterparts (pep61, pep209, pep242, pep264, pep 268; non-homologous peptides).

Figure 3:
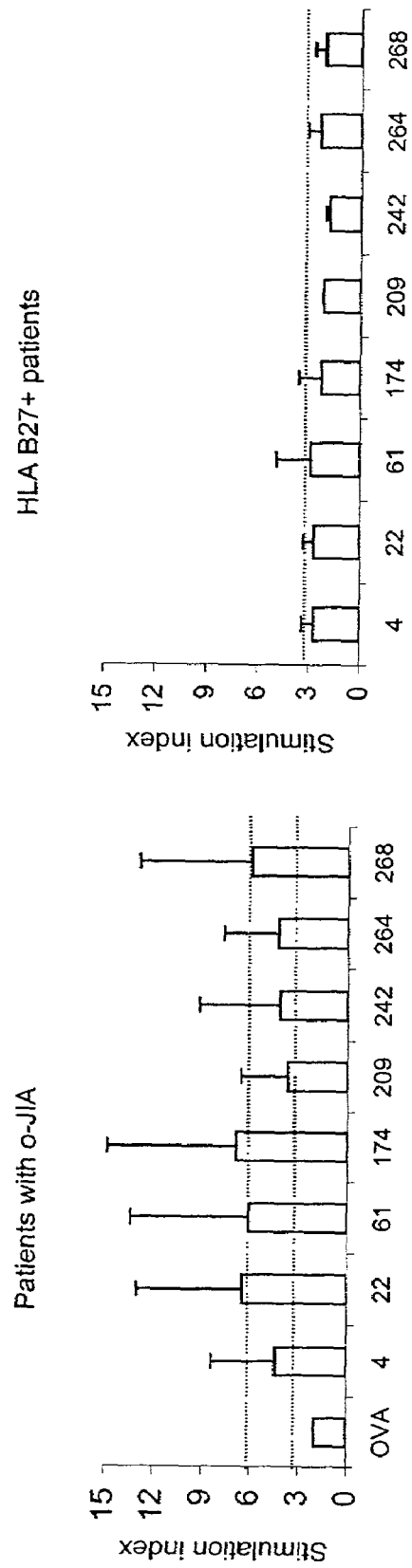
FIG. 3 shows the proliferative responses of SFMC from patients with oJIA or HLA B27+ patients incubated with recombinant *E. coli* hsp dnaJ peptides 4, 22, 61, 174, 209, 242, 264 and 268 (SEQ ID NOS: 1-8, respectively) for 72 hours, and restimulated with autologous irradiated feeder cells in presence or absence of an unrelated control peptide (OVA), or *E. coli* hsp derived peptides (as indicated). Results, expressed as stimulation index (SI), are shown as mean+SD.

The stimulation of PBMC with E. coli derived peptides resulted in very low proliferative responses (SI<1), and undetectable production of pro-inflammatory or anti-inflammatory cytokines. In contrast, SFMC proliferated in response to all of the peptides, although to a different extent, with a mean SI≧6 in the presence of peptide 22, 61, 174, or 268 (FIG. 3). To evaluate the specificity of the responses, SFMC were incubated with dnaJ, then restimulated in the presence of the unrelated OVA peptide. SFMC from HLA B27+ patients (n=4), who do not have oJIA, had a mean SI<3 in response to each of the bacterial peptides. This results suggests that the high proliferative responses to E. coli dnaJ derived peptides are disease specific.

Cytokine production to the same peptides was examined in culture supernatants of SFMC from patients with oJIA. As shown in Table 1, the production of pro-inflammatory cytokines was detectable following contact with each of the E. coli derived peptides. SFMC from only one of 21 patients with oJIA produced detectable levels of the anti-inflammatory cytokine IL-10, and none produced detectable levels of IL-4.

Among the pro-inflammatory cytokines tested, IFNγ production was significantly correlated with the proliferative responses of all of the bacterial peptides, except peptides 4 and 264 (Table 2). The correlation was stronger with peptides 22, 61, 174, and 268, which induced SI≧6, indicating that these peptides can represent relevant target epitopes at the site of inflammation. In addition, IFNγ produced in response to stimulation with peptides 209, 242, or 264 was significantly correlated to CRP and ESR values. Table 2 shows the correlation between the levels of IFNγ production in culture supernatants of SFMC from patients with oJIA stimulated with recombinant E. coli hsp dnaJ, then restimulated with irradiated autologous feeder cells in presence/absence of E. coli hsp dnaJ derived peptides, and the stimulation index (SI) induced stimulating the SFMC with the same peptides, the ESR, or the CRP values.

TABLE 2

Correlations (by Spearman test)

| Bacterial peptides | IFNγ production vs SI | IFNγ production vs ESR | IFNγ production vs CRP |
|---|---|---|---|
| 4* | NS | NS | NS |
| 22* | R = 0.55<br>p < 0.01 | NS | NS |
| 61 | R = 0.67<br>p < 0.0008 | NS | NS |

TABLE 2-continued

Correlations (by Spearman test)

| Bacterial peptides | IFNγ production vs SI | IFNγ production vs ESR | IFNγ production vs CRP |
|---|---|---|---|
| 174* | R = 0.77<br>p < 0.00001 | NS | NS |
| 209 | R = 0.50<br>p < 0.02 | R = 0.72<br>p = 0.01 | R = 0.65<br>p = 0.02 |
| 242 | R = 0.50<br>p < 0.02 | R = 0.64<br>p = 0.032 | R = 0.63<br>p = 0.03 |
| 264 | NS | R = 0.60<br>p < 0.05 | R = 0.59<br>p = 0.04 |
| 268 | R = 0.71<br>p < 0.001 | NS | NS |

*identifies bacterial peptides presenting sequence homology with peptides derived from the three human isoforms of *E. coli* hsp dnaJ.

EXAMPLE 3

Cellular Immune Responces to Human HSJ1, HDJ1, OR HDJ2 Peptides Homologous or Not Homologous to *E. coli* hsp dnaJ In order to evaluate whether human homologous peptides could be the target of cross-recognition leading to self reactivity, human peptides derived from regions of HSJ1, HDJ1, or HDJ2 having sequence homology with *E. coli* dnaJ were studied. SFMC of 14 patients with oJIA presenting a SI to the recombinant *E. coli* hsp dnaJ greater than 3 were restimulated for 96 hr with autologous cells in presence or absence of human peptide 2, 3, or 5, which are homologs of bacterial peptide 4; human peptide 20, 21, or 23, which are homologs of bacterial peptide 22; or human peptide 164, 167, or 176, which are homologs of bacterial peptide 174. SFMC proliferative responses, pro-inflammatory cytokine production, and anti-inflammatory IL-4 levels were overall similar between the peptides derived from human dnaJ proteins and the homologous bacterial peptides.

Table 3 shows the proliferative responses and cytokine production of SFMC from patients with oJIA incubated for 72 hr with recombinant *E. coli* hsp dnaJ, then restimulated with autologous irradiated feeder cells in presence or absence of *E. coli* dnaJ derived peptides or homologous peptides derived from the human dnaJ isoforms (HSJ1, HDJ1, or HDJ2). Results are expressed as SI or pg/ml (mean+SD).

TABLE 3

Proliferative responses and cytokine production

| | SI | IFNγ | TNFα | IL-6 |
|---|---|---|---|---|
| *E. coli* pep 4 | 4.1 + 3.33 | 30.8 + 52.4 | 6.0 + 4.5 | 60.2 + 60.3 |
| HSJ1 pep 2 | 5.9 + 5.7 | 51.3 + 72.4 | 23.2 + 26.8 | 41.7 + 43.8 |
| HDJ1 pep 3 | 8.0 + 7.5 | 57.5 + 85.7 | 10.3 + 9.9 | 114.0 + 126 |
| HDJ2 pep 5 | 8.2 + 7.3* | 69.5 + 105.2@ | 18.9 + 16.9 | 60.0 + 67.2 |
| *E. coli* pep 22 | 4.7 + 4.0 | 20.1 + 33.5 | 10.5 + 23.1 | 54.3 + 69.0 |
| HSJ1 pep 20 | 4.7 + 4.7 | 25.3 + 47.4 | 11.8 + 11.2 | 33.0 + 34.0 |
| HDJ1 pep 21 | 4.6 + 4.2 | 30.4 + 56.4 | 26.6 + 39.3 | 33.5 + 43.8 |
| HDJ2 pep 23 | 4.7 + 4.0 | 38.2 + 75 | 7.7 + 7.6 | 33.3 + 32.7 |
| *E. coli* pep 174 | 5.9 + 7.5 | 31.4 + 53.1 | 16.1 + 30.9 | 56.4 + 70 |
| HSJ1 pep 164 | 4.2 + 4.0 | 52.5 + 85.2 | 13.5 + 18.9 | 27.3 + 31.3 |
| HDJ1 pep 167 | 3.9 + 3.1 | 38.3 + 61.2 | 7.3 + 7.3 | 23.0 + 22.3 |
| HDJ2 pep 176 | 4.3 + 2.7 | 45.6 + 68.3 | 8.9 + 10.3 | 21.2 + 25.2 |

*p < 0.013 vs *E. coli* pep 4, @p < 0.05 vs *E. coli* pep 4

Figure 4:
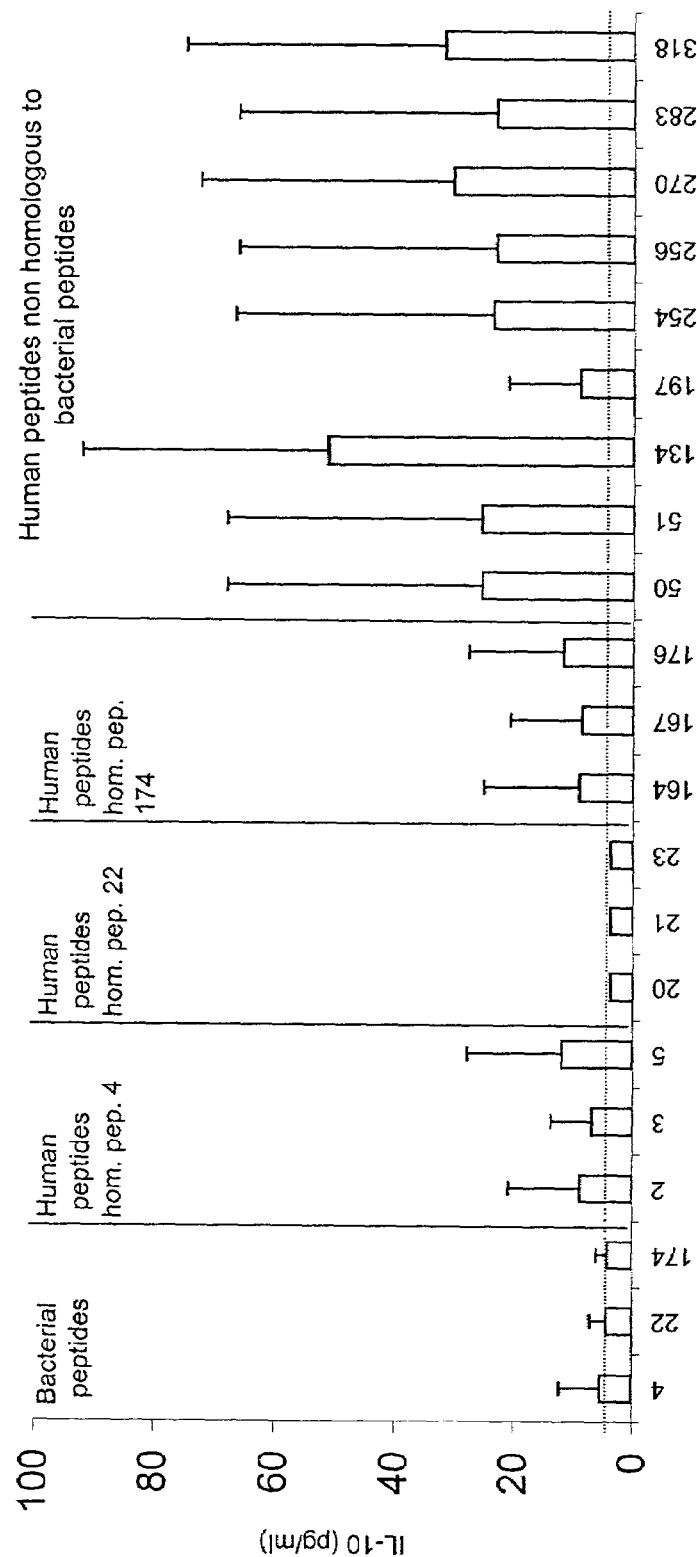
FIG. 4 shows IL-10 production in culture supernatants of SFMC from oJIA patients stimulated for 72 hours with *E. coli* hsp dnaJ peptides 4, 22 and 174 (SEQ ID NOS: 1, 2 and 4, respectively), and restimulated with autologous irradiated feeder cells presenting human peptide homologous peptides 2, 3, 5, 20, 21, 23, 164, 167, 176 (SEQ ID NOS: 9-17, respectively) or non homologous to bacterial peptides 50, 51, 134, 197, 254, 256, 270, 283 and 318 (SEQ ID NOS: 18-26, respectively). Results, expressed as pg/ml, are shown as mean+SD.
Figure 5:
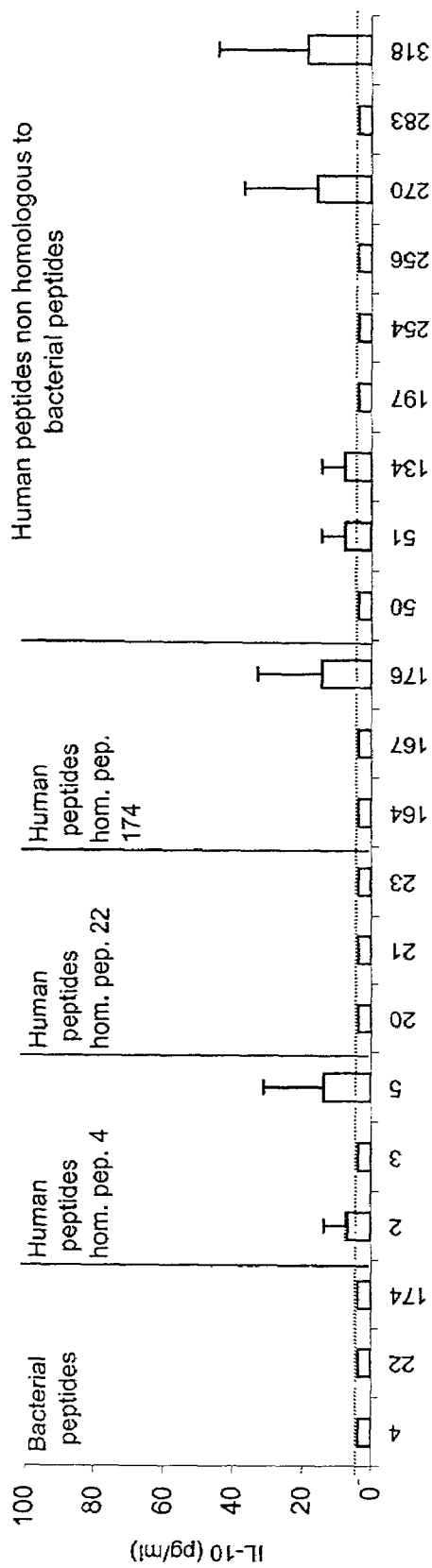
FIG. 5 shows IL-10 production in culture supernatants of SFMC from oJIA patients stimulated for 72 hours with *E. coli* hsp dnaJ 4, 22 and 174 (SEQ ID NOS: 1, 2 and 4, respectively), and restimulated with autologous irradiated feeder cells presenting homologous peptides 2, 3, 5, 20, 21, 23, 164, 167, 176 (SEQ ID NOS: 9-17, respectively) or non-homologous human peptides 50, 51, 134, 197, 254, 256, 270, 283 and 318 (SEQ ID NOS: 18-26, respectively) Results, expressed as pg/ml, are shown as mean+SD.

The only difference observed was for human peptide 5, which induced a proliferative response and IFNγ production significantly greater (p<0.03 and p<0.05, respectively) than those found in response to its bacterial homologs. Similar results were observed when the reactivity of 9 human peptides derived from regions on HSJ1, HDJ1, or HDJ2 proteins that have no sequence homology with *E. coli* hsp dnaJ was evaluated. In contrast to the results obtained with the bacterial peptides, IL-10 production was detectable, although to a different extent, in culture supernatants from SFMC stimulated with human peptides, including those homologous or non-homologous to a bacterial peptide. The mean production of IL-10 following stimulation with the non-homologous human peptides was greater (27.1±10.3 pg/ml) than with the homologous human peptides (7.7±7.0 pg/ml; FIG. 4), and was particularly evident for the homologous human peptides 20, 21, and 23, which, similar to their bacterial homolog (peptide 22), did not induce detectable levels of IL-10 (FIG. 4). These epitope mapping experiments show the different biological effects that occur with the different peptides, and that the effects are disease specific.

These results indicate that immune responses to peptides from different isoforms of human dnaJ proteins induced by the encounter with *E. coli* dnaJ can have a regulatory role through the production of anti-inflammatory IL-10, while a pro-inflammatory response to the *E. coli* hsp dnaJ can be perpetuated by bacterial peptides and homologous relevant epitopes on peptides from its human counterparts. This result was confirmed by examining the production of IL-10 in three patients presenting with extended oligoarthritis at the time of sampling, wherein culture supernatants stimulated with bacterial or human peptides showed a reduced production of IL-10, particularly with respect to human peptides 50, 254, 256, and 283, which are non-homologous with respect to *E. coli* hsp dnaJ derived peptides.

EXAMPLE 4

PROLIFERATION AND CYTOKINE PRODUCTION IN RESPONSE TO HUMAN NON-HOMOLOGOUS PEPTIDES

Figure 6:
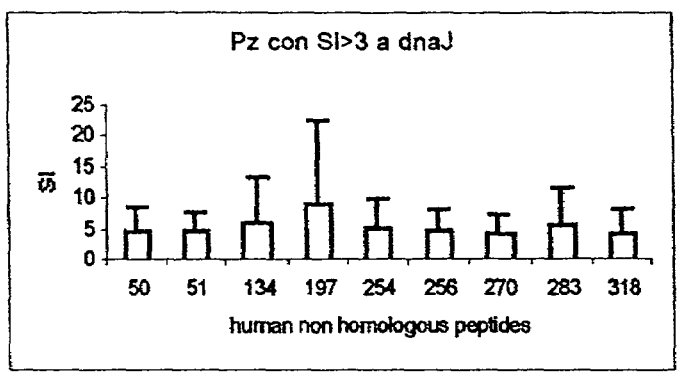
FIG. 6 shows the SI for the non-homologous human peptides 50, 51, 134, 197, 254, 256, 270, 283 and 318 (SEQ ID NOS:18-26, respectively).
Figure 7:
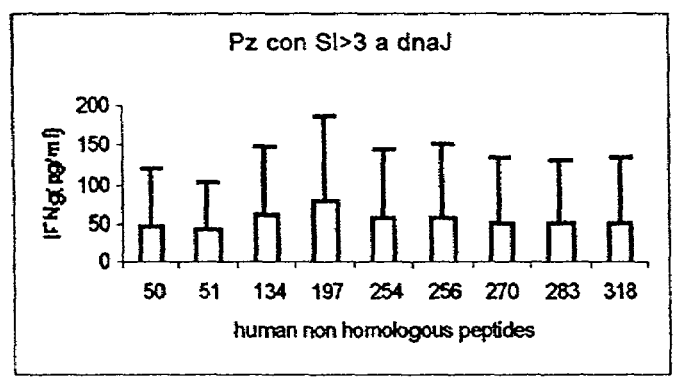
FIGS. 7 to 9 show IFNγ, TNFα, and IL-10 levels, respectively, in response to the peptides as in FIG. 6.
Figure 8:
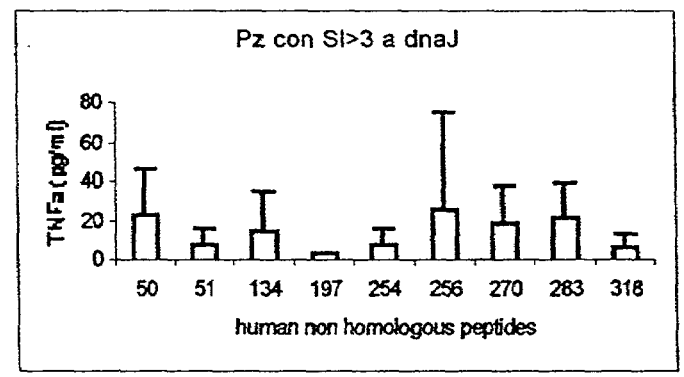
Figure 9:
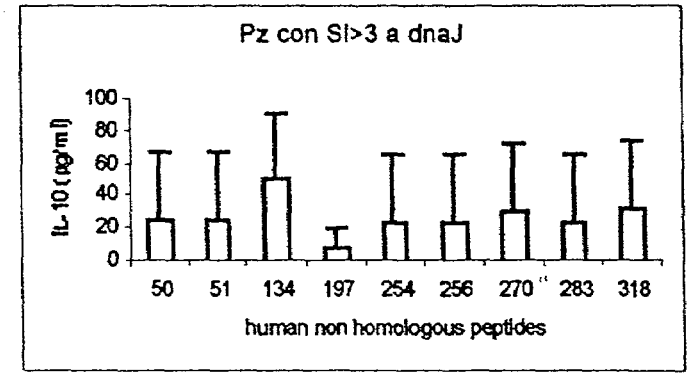

Additional peptides were tested as described above, including a series of human peptides from non-homologous regions of the isoforms of bacterial dnaJ peptides. FIG. 6 shows the SI for non-homologous peptides 50, 51, 134, 197, 254, 256, 270, 283 and 318. IFNγ, TNFα and IL-10 levels in response to these peptides are shown in FIGS. 7 to 9, respectively.

EXAMPLE 5

Figure 10:
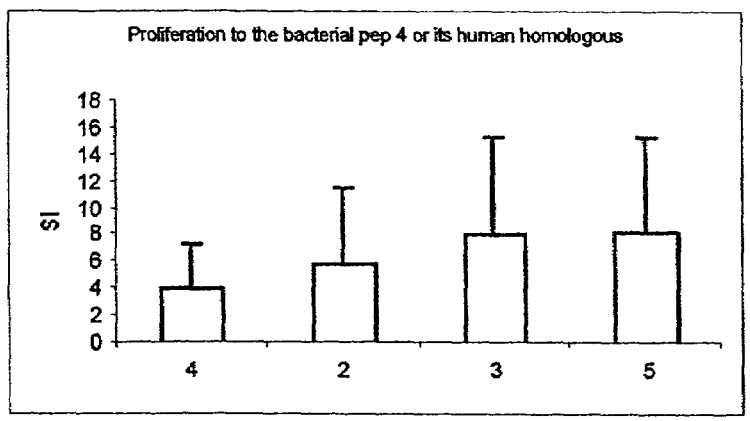
FIG. 10 shows the SI in response to bacterial dnaJ 4 (SEQ ID NO: 1) and its human homologs, 2 (SEQ ID NO:9; HSJ1), 3 (SEQ ID NO:10; HDJ1) and 5 (SEQ ID NO:11; HDJ2).
Figure 11:
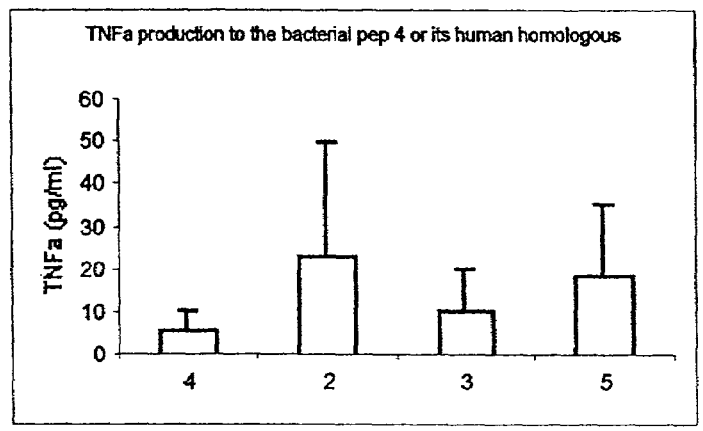
FIGS. 11 to 13 show TNFα, IFNγ, and IL-10 levels, respectively, in response to the peptides as in FIG. 10.
Figure 12:
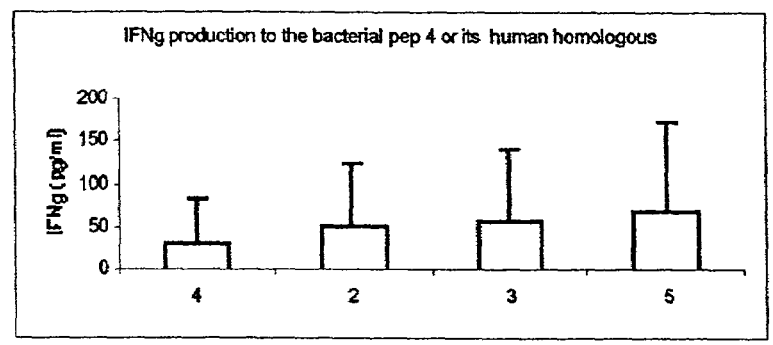
Figure 13:
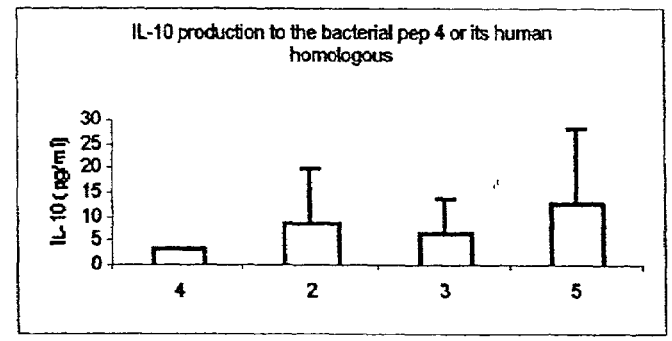
Figure 14:
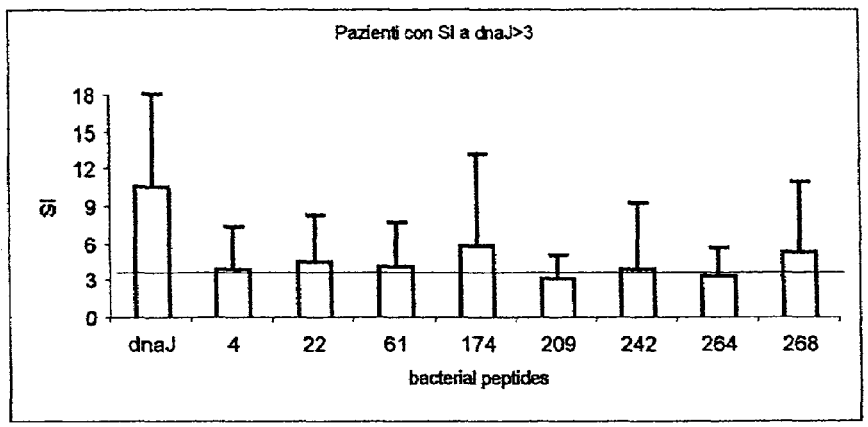
FIG. 14 shows the SI in response to bacterial peptides dnaJ, 4, 22, 61, 174, 209, 242, 264 and 268 (SEQ ID NOS:1-8, respectively).
Figure 15:
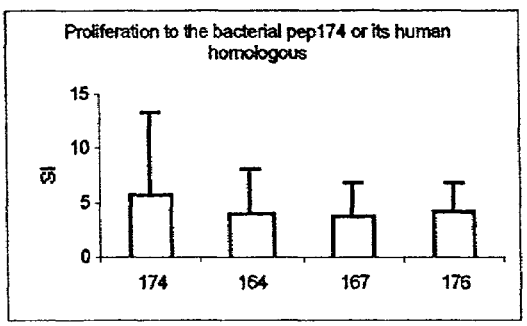
FIGS. 15 to 18 show the SI, TNFα, IFNγ, and IL-10 levels, respectively, in response to bacterial dnaJ 174 (SEQ ID NO:4) and its human homologs, 164 (SEQ ID NO:15; HSJ1), 167 (SEQ ID NO:16; HDJ2), and 176 (SEQ ID NO:17; HSJ1).
Figure 16:
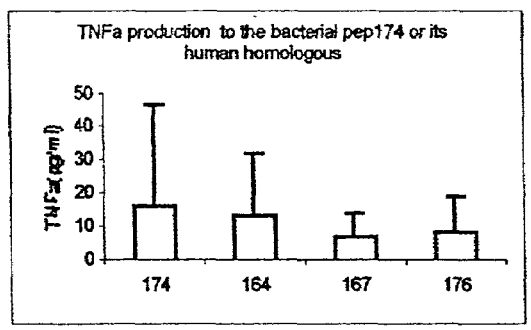
Figure 17:
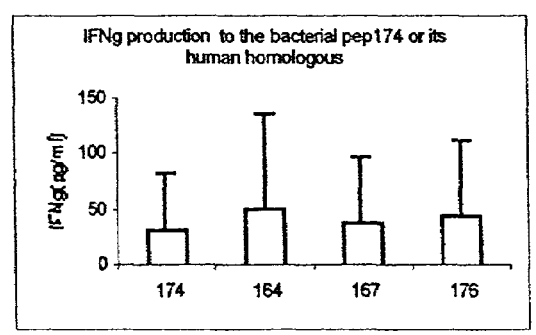
Figure 18:
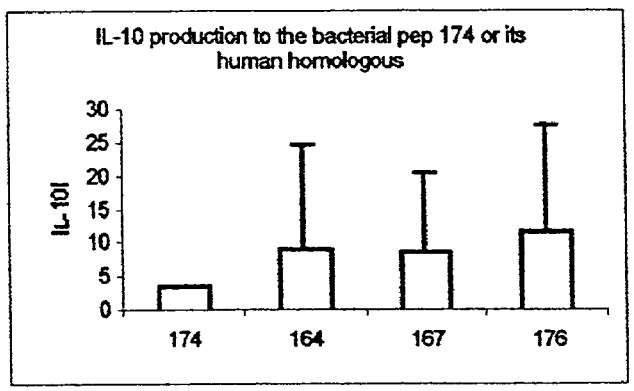
Figure 19:
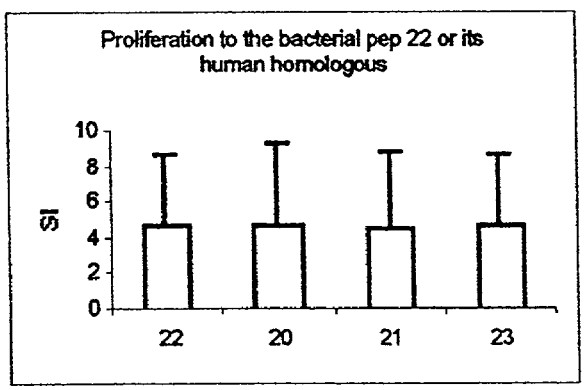
FIGS. 19 to 22 show the SI, TNFα, IFNγ, and IL-10 levels, respectively, in response to bacterial dnaj 22 (SEQ ID NO: 2) and its human homologues, 20 (HSJ 1), 21 (HDJ2), and 23 (HSJ1) (SEQ ID NOS: 12-14, respectively).
Figure 20:
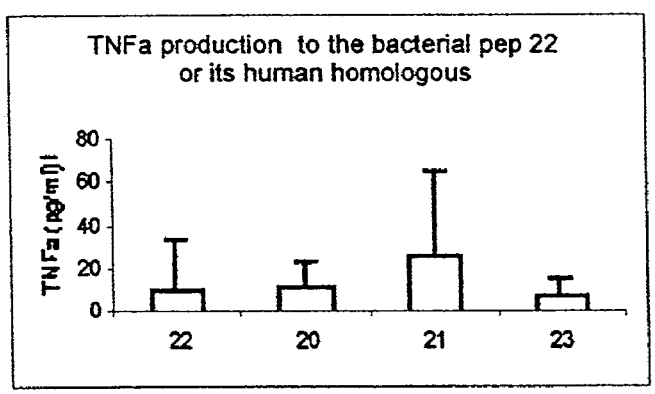
Figure 21:
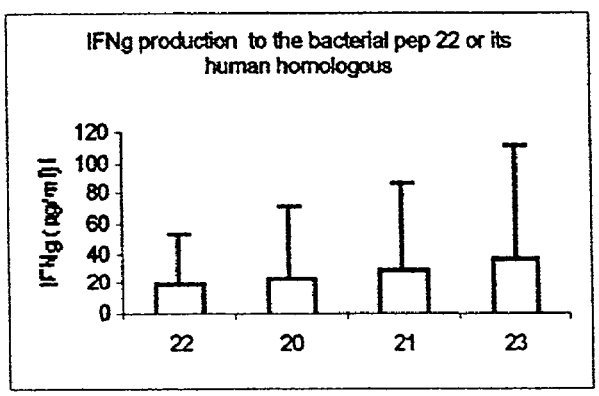
Figure 22:
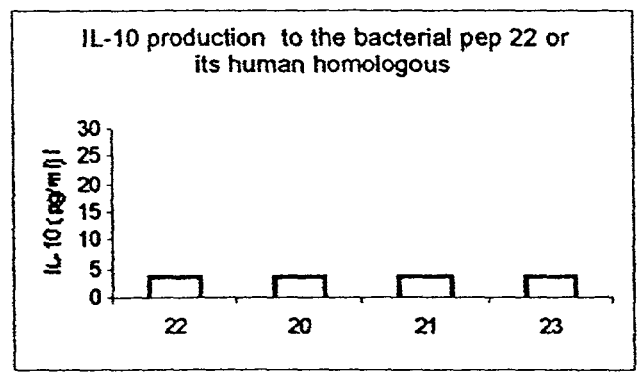

Proliferation and Cytokine Production in Responce to Bacterial Peptides and Human Homologs thereof Proliferation and cytokine production was examined in response to stimulation with various bacterial peptides, and compared to the response to stimulation with human homologs of these bacterial peptides. FIG. 10 shows the SI in response to bacterial dnaJ 4 and the human homolog peptides 2 (HSJ1), 3 (HDJ1), and 5 (HDJ2). FIGS. 11 to 13 show the TNFα, IFNγ, and IL-10 levels, respectively, in response to these peptides. The SI in response to bacterial peptides dnaJ, 4, 22, 61, 174, 209, 242, 264 and 268 is shown in FIG. 14, for comparison. FIGS. 15 to 18 show the SI, TNFα, IFNγ, and IL-10 levels, respectively, in response to bacterial dnaJ 174 and to the homologous human peptides 164 (HSJ1), 167 (HDJ2), and 176 (HSJ1). The SI, TNFα, IFNγ, and IL-10 levels in response to bacterial dnaJ 22 and the homologous human peptides 20 (HSJ1), 21 (HDJ2), and 23 (HSJ1) are shown in FIGS. 19 to 22, respectively.

EXAMPLE 6

Correlation between In Vitro Assays and Clinical Outcome

The results of the proliferation and cytokine assays (above) were compared to clinical parameters, including disease duration, erythrocyte sedimentation rate (ESR), C-reactive protein (CRP) levels, number of active joints (NAA), severity of articular index (CSA), remission interval, Children's Health Assessment Questionnaire (CHAQ), and response to treatment with dnaJ peptide ("Responders vs. non-responders"), in the same patients. As shown in Tables 4 to 10, arthritis patients who respond to dnaJ peptide therapy also showed good results as determined by the in vitro proliferation and cytokine assays using their own mononuclear cells with stimulation by peptides that are in the human isoforms only (i.e., the non-homologous human peptides). Consistent with these observations, an evaluation of patients treated with dnaJ peptides and whose arthritis had extended to more than just a few joints ("extended Pauci") revealed that the patients with extended Pauci did not respond well to the non-homologous human peptides (Table 11).

TABLE 4

Summary of Data and correlation with clinical parameters

| Patients (n = 21) | R | P |
|---|---|---|
| Spearman Disease duration vs CD69 total | −0.52 | 0.02 |
| Spearman Disease duration vs TNF pep h20 | 0.68 | 0.01 |
| Spearman ESR vs IL-10 pep h23 | 0.77 | 0.005 |

TABLE 5

C-Reactive Protein (CRP) at onset

| Spearman | R | P |
|---|---|---|
| CRP at onset vs SI pep 4 | −0.67 | 0.004 |
| CRP at onset vs TNF pep 4 | −0.59 | 0.02 |
| CRP at onset vs SI pep 209 | −0.52 | 0.037 |
| CRP at onset vs SI pep 264 | −0.51 | 0.043 |
| CRP at onset vs IL-10 pep h23 | 0.72 | 0.008 |

TABLE 5-continued

C-Reactive Protein (CRP) at onset

| Spearman | R | P |
|---|---|---|
| CRP at onset vs IL-10 pep h3 homol. pep 4 | 0.73 | 0.022 |
| CRP at onset vs IL-10 pep h5 homol. pep 4 | 0.79 | 0.011 |

TABLE 6

Number of active joints (NAA)

| Spearman | R | P |
|---|---|---|
| NAA vs IL-10 pep h164 | 0.62 | 0.022 |

TABLE 7

Severity Articular Index (CSA)

| Spearman | R | P |
|---|---|---|
| CSA vs SI dnaJ | 0.51 | 0.02 |
| CSA vs SI h50 nonhomol. | 0.75 | 0.018 |
| CSA vs TNF pep 242 | 0.48 | 0.03 |

TABLE 8

Responders vs. Non-responders a 6 Months

Mann-Whitney

| | | |
|---|---|---|
| Res. at 6 months vs SI pep 268 | 0.049 | |
| Res. at b months vs SI h167 omol. 174 | 0.037 | > responders |
| Res. at 6 months vs IFN 174 | 0.012 | > responders |
| Res. at 6 months vs SI h20 homol. 22 | | > responders |
| Res. at 6 months vs IFN 22 | | > responders |
| Res. at 6 months vs SI h270 nonhomol. | 0.034 | > responders |
| Res. at 6 months vs IFN 4 | 0.034 | > responders |
| Res. at 6 months vs IL-10 a dnaJ | 0.024 | > non-responders |

TABLE 9

Remission interval (Rem int.)

| Spearman | R | P |
|---|---|---|
| Rem int. vs SI dnaJ | 0.53 | 0.049 |
| Rem int. vs SI 174 | 0.6 | 0.021 |
| Rem int. vs SI 209 | 0.61 | 0.02 |
| Rem int. vs SI 268 | 0.56 | 0.038 |
| Rem int. vs IFN 174 | 0.68 | 0.019 |
| Rem int. vs IFN 22 | 0.71 | 0.009 |

TABLE 10

Children Health Assessment Questionnaire (CHAQ)

| | R | P |
|---|---|---|
| CHAQ vs SI dnaJ | −0.49 | 0.037 |
| CHAQ vs SI 174 | −0.63 | 0.005 |
| CHAQ vs ST 268 | −0.56 | 0.015 |
| CHAQ vs ST 209 | −0.5 | 0.032 |
| CHAQ vs SI h20 | −0.54 | 0.043 |
| CHAQ vs IFN dnaJ | −0.56 | 0.017 |
| CHAQ vs IFN 174 | −0.61 | 0.006 |
| CHAQ vs IFN 268 | −0.59 | 0.009 |

TABLE 10-continued

Children Health Assessment Questionnaire (CHAQ)

| | R | P |
|---|---|---|
| CHAQ vs IFN 22 | −0.6 | 0.0076 |
| CHAQ vs IFN 61 | −0.56 | 0.015 |
| CHAQ vs IFN h167 (homol. 174) | −0.59 | 0.04 |
| CHAQ vs TNF 174 | −0.57 | 0.011 |
| CHAQ vs TNF 22 | −0.57 | 0.011 |
| CHAQ vs IFNγ Hu. nonhomol. 50 | −0.49 | 0.036 |
| CHAQ vs IFNγ Hu. nonhomol. 51 | −0.5 | 0.034 |
| CHAQ vs IFNγ Hu. nonhomol. 134 | −0.49 | 0.036 |
| CHAQ vs IFNγ Hu. nonhomol. 197 | −0.6 | 0.01 |
| CHAQ vs IFNγ Hu. nonhomol. 254 | −0.49 | 0.036 |
| CHAQ vs IFNγ Hu. nonhomol. 256 | −0.49 | 0.036 |
| CHAQ vs IFNγ Hu. nonhomol. 270 | −0.49 | 0.036 |
| CHAQ vs IFNγ Hu. nonhomol. 283 | −0.49 | 0.036 |
| CHAQ vs IFNγ Hu. nonhomol. 318 | −0.5 | 0.034 |

TABLE 11

Pauci Patients Compared to Extended Pauci Patients
Pauci (n = 14) vs. Pauci ext (n = 7)

| Mann Whitney | |
|---|---|
| IFNγ 22 | 0.033 |
| IFNγ 174 | 0.427 |
| IFNγ h164 homol. 174 | 0.037 |
| IFNγ h167 homol. 174 | 0.037 |
| IFNγ h176 homol. 174 | 0.037 |
| IFNγ 22 | 0.032 |
| IFNγ 268 | 0.044 |

EXAMPLE 7

Figure 23:
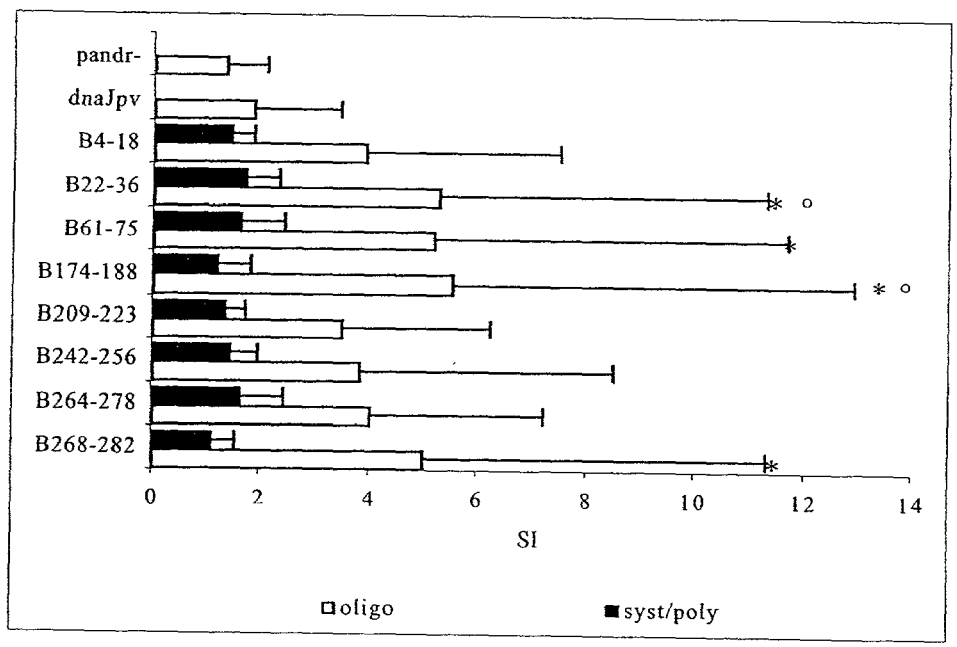
FIG. 23 shows the proliferative responses to bacterial dnaJ peptides 4, 22, 61, 174, 209, 242, 264 and 268 (SEQ ID NOS: 1-8, respectively) in patients with oJIA ("oligo") as compared to patients with forms of JIA other than oJIA ("syst/poly"). Results are expressed as SI (bars indicate SD). pandr and dnaJpv are control peptides.

Immune Responces to Bacterial HSP dnaJ Epitopes in Synovial Fluid Mononuclear Cells of oJIA Patients T cell responses against the whole *E. coli* dnaJ heat shock protein were predominantly of TH-1 type and confined to the synovial fluid compartment. T cell proliferation (SI) and IFN production were significantly elevated when SFMC responses from oJIA patients were compared to PBMC from the same source. Responses from SFMC of oJIA patients were significantly elevated than SFMC from disease controls, including 14 patients with systemic and polyarticular JIA, for four out of eight pan-DR binder peptides of bacterial dnaJ origin tested as T cell antigens (FIG. 23). These responses were also of pro-inflammatory nature, as underscored by the production of IFN and the undetectable levels of regulatory cytokines in responses to individual peptides in vitro. Such reactivity was compartment, antigen and disease specific, as PBMC and SFMC from 14 patients with different types of JIA, as well as age matched healthy controls, showed only negligible responses.

Significant differences were found when reactivity to the proband antigens was compared with control irrelevant peptides, including a pan DR binder designer peptide (pandr), and an *E coli* derived altered peptide ligand (dna-Jpv; see FIG. 23). Increased response of SFMC to recombinant dnaJ was not secondary to a non-specific increase in SFMC reactivity. In 7 patients with oJIA, the proliferative responses of cells from both compartments to tetanus toxoid (TT), an unrelated memory antigen, also was tested. In order to compare the differences in the responses of PBMC and SFMC to recombinant dnaJ and TT, the ratio of the stimulation index obtained in the two compartments for each of the two antigens was calculated. The ratio SI SFMC/SI PBMC was significantly (p<0.02) greater following stimulation with the recombinant dnaJ than with TT.

These results demonstrate a marked reactivity to *E. coli* dnaJ epitopes in the synovial compartment of patients with o-JIA, indicating that this response may have a role at the site of inflammation. Such role can be related to modulation of autoimmune inflammation, and can be based on an interplay among different epitopes on the bacterial protein and its human equivalents, which may be overexpressed at the synovial site. As such, the identity of such putative epitopes was examined.

Since 2 of the 4 immunogenic bacterial peptides (22 and 174) were derived from regions on *E. coli* hsp dnaJ having sequence homology with human dnaJ proteins (HSJ1, HDJ1, or HDJ2), the possibility of cross recognition leading to self reactivity was evaluated. Homologous human peptides 20, 21, and 23 (homologs of bacterial peptide 22) and peptides 164, 167-181, and 176 (homologs of bacterial peptide 174), and non-homologous human peptides, were examined. These peptides elicited T cell reactivity, with proliferation and production of IFNγ comparable to those obtained following stimulation with the corresponding homologous bacterial peptides. SI and IFNγ responses to these human peptides were highly correlated to those obtained in presence of the bacterial homologues. These results demonstrate a correlation between the T cell responses to bacterial peptides and their human homologs via cross-recognition. In contrast with the results obtained with bacterial peptides, detectable levels of IL-10 were detected in culture supernatants of SFMC stimulated with peptides derived from human dnaJ peptides; IL-4 was undetectable. The results further demonstrate that self antigens can trigger a qualitatively different T cell response.

Figure 24A:
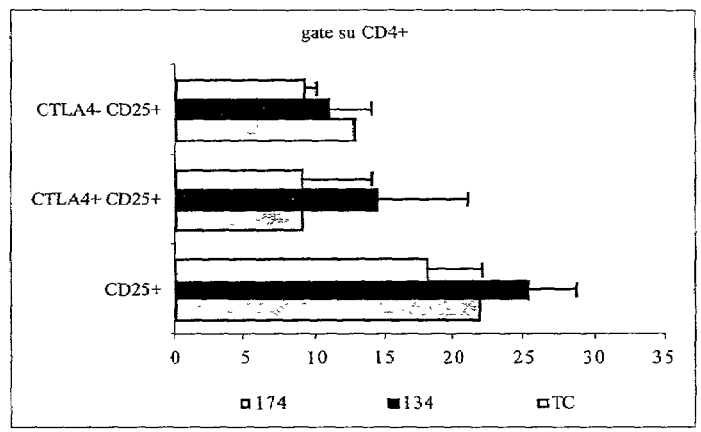
FIG. 24A shows the percent of CTLA4/CD25 positive cells in response to stimulation with peptides 174 and 134 (SEQ ID NOS: 4 and 20, respectively). "TC" indicates tissue culture not stimulated. Bars represent SD.
Figure 24B:
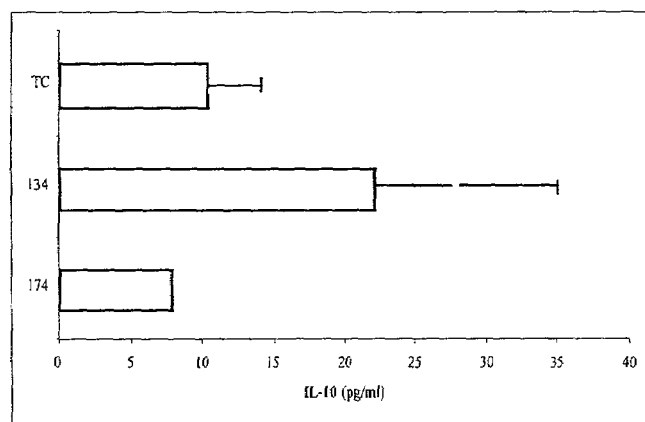
FIG. 24B shows IL-10 production by SFMC of oJIA patients stimulated with peptides 174 and 134 (SEQ ID NOS: 4 and 20, respectively), expressed as pg/ml.

FACS analysis was used to evaluate the percent of CTLA+/CD25/CD4 positive cells following stimulation of representative SFMC from patients with persistent oJIA with non-homologous human peptide 134. The % of CTLA+/CD25/CD4 positive cells, which are believed to have a regulatory function, was higher in the peptide treated cells as compared to cells maintained under control conditions (FIG. 24A). Expansion of the regulatory cells in response to peptide 134 correlated well with production of IL-10 in the same culture conditions (FIG. 24B). These results demonstrate that recognition of the human dnaJ 134 peptide leads to expansion of regulatory cells and production of IL-10.

Figure 25A:
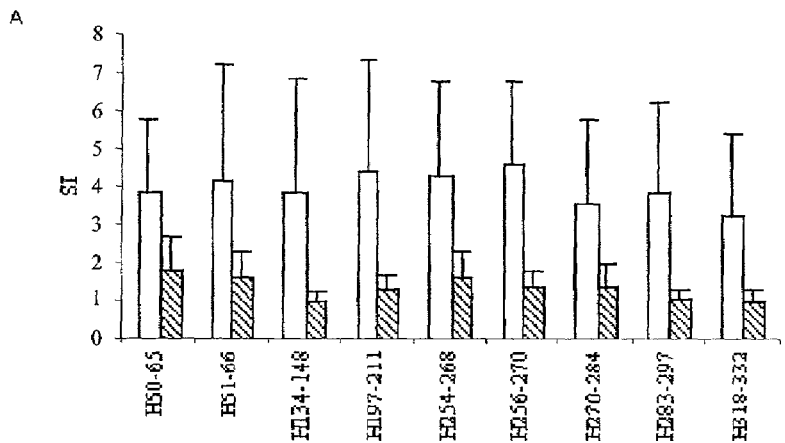
FIGS. 25A to 25C show the proliferative response (SI.
Figure 25B:
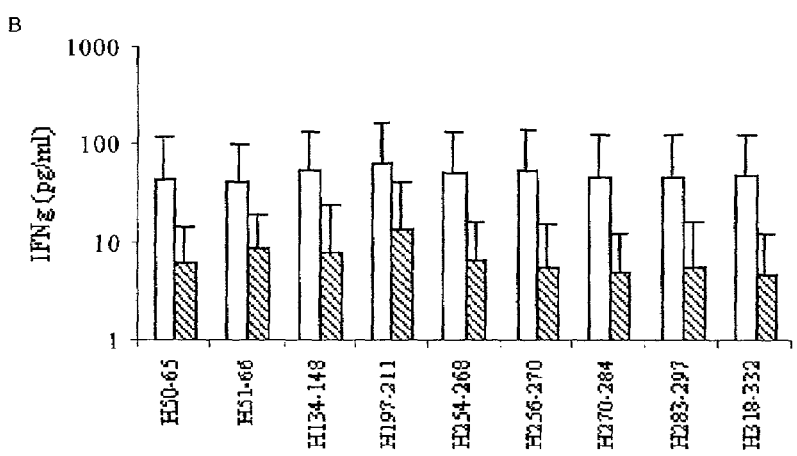
Figure 25C:
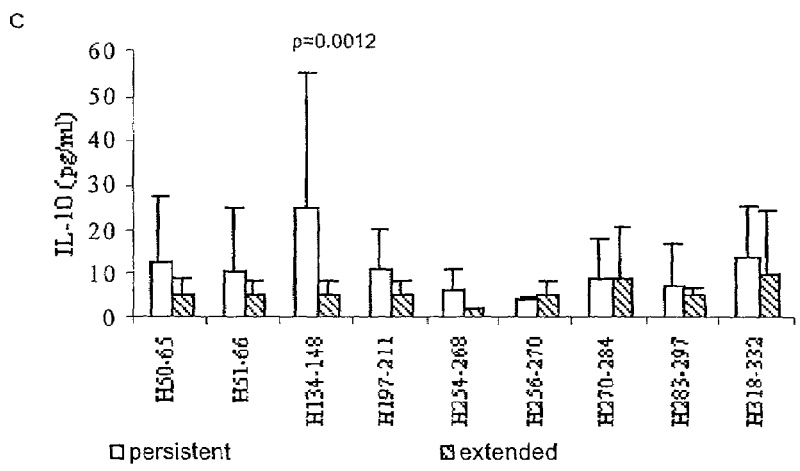

To explore the possible correlation of clinical features with the development of peptide-induced immune modulation, oJIA patients were grouped according to the course of disease, including those with persistent disease (n=16), and those with extended disease (n=15) o-JIA. (FIG. 25). Proliferative responses to peptide 134 were significantly lower (p=0.05) in samples from patients with extended disease as compared to those with persistent o-JIA (FIGS. 25A and 25B). In addition, a border line level of statistical significance (p=0.076) was observed with respect to IFN production. A highly significant difference was found when IL-10 production was considered (p=0.0012; see FIG. 25C).

In order to further analyze possible associations with a more benign disease, the duration of the clinical remission of the studied joint following intraarticular administration of an injectable steroid, TXA, was considered as a measure of the degree of inflammatory activity in individual joints. IL-10 production in response to the non-homologous human peptide 134 was highly correlated with the duration of the clinical remission of individual joint (R=0.537, p=0.026).

These results indicate that recognition of immunomodulatory self epitopes is associated with remitting disease.

EXAMPLE 8 dnaJP1 Peptide Provides a Pro-Inflammatory Epitope in Patients with Rheumatoid Arthritis A peptide from the hsp dnaJ protein that acts as a trigger of T cell proliferation and production of pro-inflammatory cytokines from peripheral blood and synovial fluid cells of rheumatoid arthritis (RA) patients was identified. This peptide, dnaJ P1 (QKRAAYDQYGHAAFE; SEQ ID NO:27), shares sequence homology with the "shared epitope", which is a five amino acid stretch in common among RA associated HLA alleles (Albani et al., Nat. Med. 1:448-52, 1995, which is incorporated herein by reference). A study was performed to determine whether, in RA an interplay between HLA and dnaJ derived peptides maintains and stimulates T cells, which participate in autoimmune inflammation. Such a population of T cells has been the target of a Phase I Immune Tolerization study.

Figures 26D, 26E:
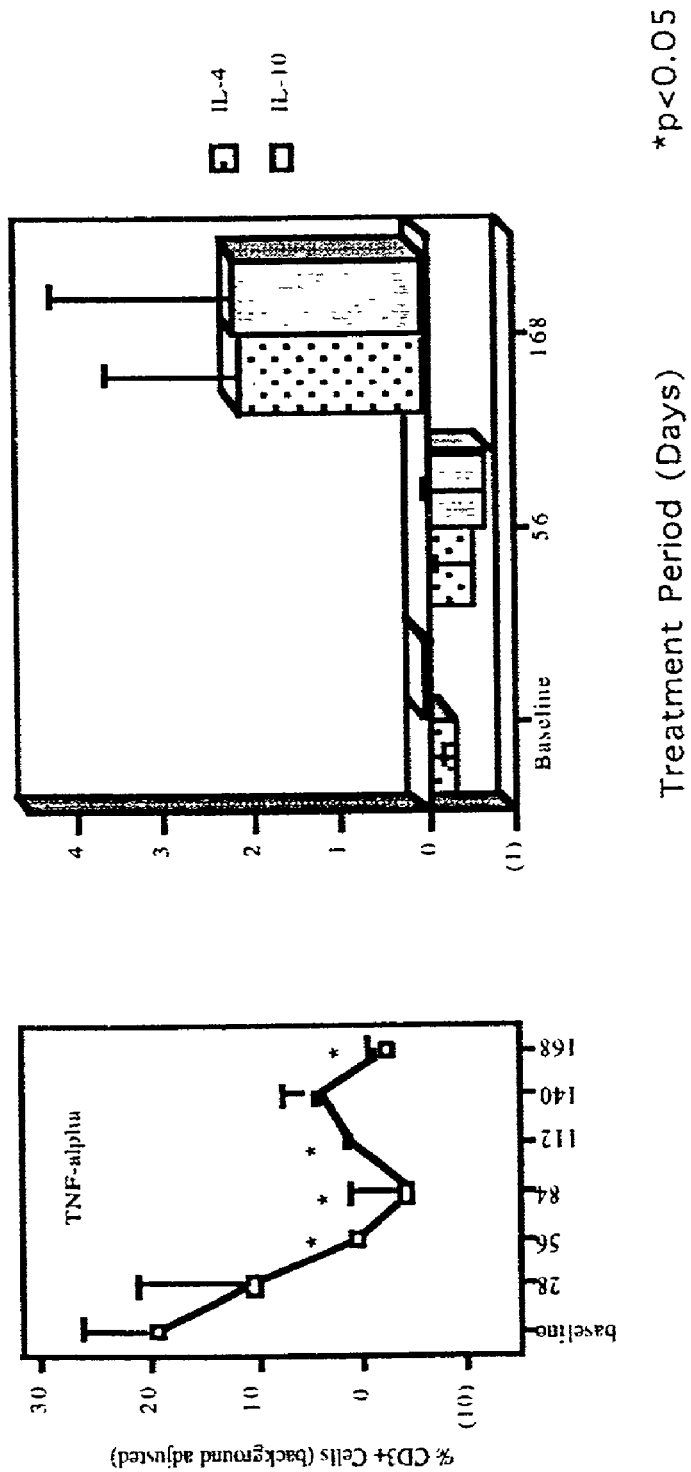

In the Phase I clinical trial, 15 RA patients were treated with three different doses of dnaJP1 (four times per day, by mouth) for 6 months. Entry criteria required clinically active disease and pro-inflammatory T cell responsiveness in vitro to the peptide. As shown in FIG. 26, mucosal tolerization to dnaJP1 induced a dramatic immune deviation from pro-inflammatory to regulatory-type cytokines. The immune changes were treatment specific and treatment induced.

Although the invention has been described with reference to the above example, it will be understood that modifications and variations are encompassed within the spirit and scope of the invention. Accordingly, the invention is limited only by the following claims.

What is claimed is:

1. A substantially purified peptide consisting of an amino acid sequence selected from the group consisting of SEQ ID NOs: 1 to 18, 20 to 25 and 26.

2. A composition, comprising at least one peptide of claim 1 and a pharmaceutically acceptable carrier.

3. The composition of claim 2, further comprising an immunoadjuvant.

4. The composition of claim 3, wherein the immunoadjuvant is a cytokine.

5. The composition of claim 3, wherein the immunoadjuvant is selected from the group consisting of Freund's complete adjuvant, Freund's incomplete adjuvant, and alum.

* * * * *

SEQUENCE LISTING

```
<160> NUMBER OF SEQ ID NOS: 27

<210> SEQ ID NO 1
<211> LENGTH: 15
<212> TYPE: PRT
<213> ORGANISM: Escherichia coli

<400> SEQUENCE: 1

Gln Asp Tyr Tyr Glu Ile Leu Gly Val Ser Lys Thr Ala Glu Glu
1               5                   10                  15

<210> SEQ ID NO 2
<211> LENGTH: 15
<212> TYPE: PRT
<213> ORGANISM: Escherichia coli

<400> SEQUENCE: 2

Arg Lys Ala Tyr Lys Arg Leu Ala Met Lys Tyr His Pro Asp Arg
1               5                   10                  15

<210> SEQ ID NO 3
<211> LENGTH: 16
<212> TYPE: PRT
<213> ORGANISM: Escherichia coli

<400> SEQUENCE: 3

Gln Lys Arg Ala Ala Tyr Asp Gln Tyr Gly His Ala Ala Phe Glu Gln
1               5                   10                  15

<210> SEQ ID NO 4
<211> LENGTH: 15
<212> TYPE: PRT
<213> ORGANISM: Escherichia coli

<400> SEQUENCE: 4

Gln Gly Phe Phe Ala Val Gln Gln Thr Cys Pro His Cys Gln Gly
1               5                   10                  15

<210> SEQ ID NO 5
<211> LENGTH: 15
<212> TYPE: PRT
<213> ORGANISM: Escherichia coli

<400> SEQUENCE: 5
```

-continued

```
Ser Lys Thr Leu Ser Val Lys Ile Pro Gly Ala Val Asp Thr Gly
1               5                   10                  15
```

<210> SEQ ID NO 6
<211> LENGTH: 15
<212> TYPE: PRT
<213> ORGANISM: Escherichia coli

<400> SEQUENCE: 6

```
Gly Asp Leu Tyr Val Gln Val Gln Val Lys Gln His Pro Ile Phe
1               5                   10                  15
```

<210> SEQ ID NO 7
<211> LENGTH: 15
<212> TYPE: PRT
<213> ORGANISM: Escherichia coli

<400> SEQUENCE: 7

```
Tyr Cys Glu Val Pro Ile Asn Phe Ala Met Ala Ala Leu Gly Gly
1               5                   10                  15
```

<210> SEQ ID NO 8
<211> LENGTH: 15
<212> TYPE: PRT
<213> ORGANISM: Escherichia coli

<400> SEQUENCE: 8

```
Pro Ile Asn Phe Ala Met Ala Ala Leu Gly Gly Glu Ile Glu Val
1               5                   10                  15
```

<210> SEQ ID NO 9
<211> LENGTH: 15
<212> TYPE: PRT
<213> ORGANISM: Homo sapiens

<400> SEQUENCE: 9

```
Ala Ser Tyr Tyr Glu Ile Leu Asp Val Pro Arg Ser Ala Ser Ala
1               5                   10                  15
```

<210> SEQ ID NO 10
<211> LENGTH: 15
<212> TYPE: PRT
<213> ORGANISM: Homo sapiens

<400> SEQUENCE: 10

```
Lys Asp Tyr Tyr Gln Thr Leu Gly Leu Ala Arg Gly Ala Ser Asp
1               5                   10                  15
```

<210> SEQ ID NO 11
<211> LENGTH: 15
<212> TYPE: PRT
<213> ORGANISM: Homo sapiens

<400> SEQUENCE: 11

```
Thr Thr Tyr Tyr Asp Val Leu Gly Val Lys Pro Asn Ala Thr Gln
1               5                   10                  15
```

<210> SEQ ID NO 12
<211> LENGTH: 15
<212> TYPE: PRT
<213> ORGANISM: Homo sapiens

<400> SEQUENCE: 12

```
Lys Lys Ala Tyr Arg Arg Lys Ala Leu Gln Trp His Pro Asp Lys
1               5                   10                  15
```

<210> SEQ ID NO 13
<211> LENGTH: 15
<212> TYPE: PRT
<213> ORGANISM: Homo sapiens

<400> SEQUENCE: 13

Lys Arg Ala Tyr Arg Arg Gln Ala Leu Arg Tyr His Pro Asp Lys
1               5                   10                  15

<210> SEQ ID NO 14
<211> LENGTH: 15
<212> TYPE: PRT
<213> ORGANISM: Homo sapiens

<400> SEQUENCE: 14

Lys Lys Ala Tyr Arg Lys Leu Ala Leu Lys Tyr His Pro Asp Lys
1               5                   10                  15

<210> SEQ ID NO 15
<211> LENGTH: 15
<212> TYPE: PRT
<213> ORGANISM: Homo sapiens

<400> SEQUENCE: 15

Phe Arg Ser Val Ser Thr Ser Thr Thr Phe Val Gln Gly Arg Arg
1               5                   10                  15

<210> SEQ ID NO 16
<211> LENGTH: 15
<212> TYPE: PRT
<213> ORGANISM: Homo sapiens

<400> SEQUENCE: 16

Pro Gly Met Val Gln Gln Ile Gln Ser Val Cys Met Glu Cys Gln
1               5                   10                  15

<210> SEQ ID NO 17
<211> LENGTH: 15
<212> TYPE: PRT
<213> ORGANISM: Homo sapiens

<400> SEQUENCE: 17

Gly Arg Arg Ile Thr Thr Arg Arg Ile Met Glu Asn Gly Gln Glu
1               5                   10                  15

<210> SEQ ID NO 18
<211> LENGTH: 16
<212> TYPE: PRT
<213> ORGANISM: Homo sapiens

<400> SEQUENCE: 18

Gln Ala Tyr Glu Val Leu Ser Asp Ala Lys Lys Arg Glu Leu Tyr Asp
1               5                   10                  15

<210> SEQ ID NO 19
<211> LENGTH: 16
<212> TYPE: PRT
<213> ORGANISM: Homo sapiens

<400> SEQUENCE: 19

Glu Ala Tyr Glu Val Leu Ser Asp Lys His Lys Arg Glu Ile Tyr Asp
1               5                   10                  15

-continued

```
<210> SEQ ID NO 20
<211> LENGTH: 15
<212> TYPE: PRT
<213> ORGANISM: Homo sapiens

<400> SEQUENCE: 20

Ser Gly Pro Phe Phe Thr Phe Ser Ser Ser Phe Pro Gly His Ser
1               5                   10                  15

<210> SEQ ID NO 21
<211> LENGTH: 15
<212> TYPE: PRT
<213> ORGANISM: Homo sapiens

<400> SEQUENCE: 21

Asp Gly Gln Leu Lys Ser Val Thr Ile Asn Gly Val Pro Asp Asp
1               5                   10                  15

<210> SEQ ID NO 22
<211> LENGTH: 15
<212> TYPE: PRT
<213> ORGANISM: Homo sapiens

<400> SEQUENCE: 22

Asp Leu Gln Leu Ala Met Ala Tyr Ser Leu Ser Glu Met Glu Ala
1               5                   10                  15

<210> SEQ ID NO 23
<211> LENGTH: 15
<212> TYPE: PRT
<213> ORGANISM: Homo sapiens

<400> SEQUENCE: 23

Glu Asp Leu Phe Met Cys Met Asp Ile Gln Leu Val Glu Ala Leu
1               5                   10                  15

<210> SEQ ID NO 24
<211> LENGTH: 15
<212> TYPE: PRT
<213> ORGANISM: Homo sapiens

<400> SEQUENCE: 24

Leu Cys Gly Phe Gln Lys Pro Ile Ser Thr Leu Asp Asn Arg Thr
1               5                   10                  15

<210> SEQ ID NO 25
<211> LENGTH: 15
<212> TYPE: PRT
<213> ORGANISM: Homo sapiens

<400> SEQUENCE: 25

Arg Thr Ile Val Ile Thr Ser His Pro Gly Gln Ile Val Lys His
1               5                   10                  15

<210> SEQ ID NO 26
<211> LENGTH: 15
<212> TYPE: PRT
<213> ORGANISM: Homo sapiens

<400> SEQUENCE: 26

Gly Arg Leu Ile Ile Glu Phe Lys Val Asn Phe Pro Glu Asn Gly
1               5                   10                  15
```

```
<210> SEQ ID NO 27
<211> LENGTH: 15
<212> TYPE: PRT
<213> ORGANISM: Escherichia coli

<400> SEQUENCE: 27

Gln Lys Arg Ala Ala Tyr Asp Gln Tyr Gly His Ala Ala Phe Glu
1               5                   10                  15
```